(12) United States Patent
Mitra et al.

(10) Patent No.: US 11,630,035 B2
(45) Date of Patent: Apr. 18, 2023

(54) METHOD, SYSTEM, AND DEVICE FOR AUTOMATING TRANSFER OF TAPE TO MICROTOME SECTIONS

(71) Applicant: Clarapath, Inc., New York, NY (US)

(72) Inventors: Partha P. Mitra, New York, NY (US); Alexander S. Tolpygo, South Setauket, NY (US); Robert L. Kleinberg, Cambridge, MA (US)

(73) Assignee: Clarapath, Inc., Hawthorne, NY (US)

( * ) Notice: Subject to any disclaimer, the term of this patent is extended or adjusted under 35 U.S.C. 154(b) by 505 days.

(21) Appl. No.: 16/671,385

(22) Filed: Nov. 1, 2019

(65) Prior Publication Data

US 2020/0064232 A1 Feb. 27, 2020

Related U.S. Application Data

(63) Continuation of application No. 15/179,916, filed on Jun. 10, 2016, now Pat. No. 10,473,557.

(Continued)

(51) Int. Cl.
*G01N 35/00* (2006.01)
*G01N 1/06* (2006.01)
(Continued)

(52) U.S. Cl.
CPC ......... *G01N 1/06* (2013.01); *G01N 33/48764* (2013.01); *G01N 35/00009* (2013.01); *G01N 2001/362* (2013.01); *G01N 2035/00019* (2013.01); *G01N 2035/00108* (2013.01); *G01N 2203/0282* (2013.01)

(58) Field of Classification Search
CPC .............. G01N 1/06; G01N 2001/362; G01N 2035/00019; G01N 2035/00108; G01N 2203/0282; G01N 33/48764; G01N 35/00009
See application file for complete search history.

(56) References Cited

U.S. PATENT DOCUMENTS 3,552,247 A 1/1971 Pickett
3,667,330 A 6/1972 Kobernick
(Continued)

FOREIGN PATENT DOCUMENTS

JP 2008/216109 9/2008
WO WO 2012/033842 3/2012

OTHER PUBLICATIONS

Palmgren, Axel. "Tape for Microsectioning of Very Large, Hard or Brittle Specimens." Nature 174.4418 (1954): 46. Web.
(Continued)

*Primary Examiner* — Benjamin R Whatley
(74) *Attorney, Agent, or Firm* — Greenberg Traurig, LLP; David J. Dykeman; Roman Fayerberg

(57) ABSTRACT

A system and method for automated transfer of a tape segment onto the face of a tissue block to be thin sectioned by microtomy includes applying, to a carrier strip, a plurality of serially-spaced patches of sample tape having an adhesive outer surface, transporting the carrier strip along a path adjacent to and spaced from the exposed sample surface to position one of the patches of sample tape adjacent to and covering the exposed sample surface, adhering the one of the patches of sample tape to the exposed sample surface.

12 Claims, 17 Drawing Sheets

Related U.S. Application Data

(60) Provisional application No. 62/187,114, filed on Jun. 30, 2015.

(51) Int. Cl.
  *G01N 33/487* (2006.01)
  *G01N 1/36* (2006.01)

(56) References Cited

U.S. PATENT DOCUMENTS

| | | |
|---|---|---|
| 3,690,933 A | 9/1972 | Cole |
| 3,690,988 A | 9/1972 | Ullberg et al. |
| 3,832,923 A | 9/1974 | Lassmann et al. |
| 3,939,019 A | 2/1976 | Pickett |
| 4,190,472 A | 2/1980 | Slonicki |
| 4,257,346 A | 3/1981 | Ornstein et al. |
| 4,264,560 A | 4/1981 | Natelson |
| 4,545,831 A | 10/1985 | Ornstein |
| 4,752,347 A | 6/1988 | Rada |
| 4,883,642 A | 11/1989 | Bisconte |
| 5,156,019 A | 10/1992 | McCormick |
| 5,444,105 A | 8/1995 | Ornstein |
| 5,480,508 A | 1/1996 | Manabe et al. |
| 5,713,255 A | 2/1998 | Izvozichikov et al. |
| 5,740,708 A | 4/1998 | Tabone |
| 5,746,855 A | 5/1998 | Bolles |
| 5,958,341 A | 9/1999 | Chu |
| 6,253,653 B1 | 7/2001 | Walter et al. |
| 6,330,348 B1 | 12/2001 | Kerschmann et al. |
| 6,387,653 B1 | 5/2002 | Voneiff et al. |
| 6,568,307 B1 | 5/2003 | Gunther et al. |
| 6,598,507 B1 | 7/2003 | Gunther et al. |
| 6,634,268 B1 | 10/2003 | Guenther et al. |
| 6,715,870 B2 | 4/2004 | Kiene et al. |
| 6,720,191 B1 | 4/2004 | Goldstein |
| 7,374,907 B1 | 5/2008 | Voneiff et al. |
| 7,503,245 B2 | 3/2009 | Miyazawa et al. |
| 7,677,289 B2 | 3/2010 | Hayworth et al. |
| 7,811,518 B2 | 10/2010 | Kokubo |
| 7,866,464 B2 | 1/2011 | Miyatani et al. |
| 7,966,091 B2 | 6/2011 | Fujimoto et al. |
| 8,048,206 B2 | 11/2011 | Schmitt et al. |
| 8,051,760 B2 | 11/2011 | Walter |
| 8,056,456 B2 | 11/2011 | Walter |
| 8,074,547 B2 | 12/2011 | Ito et al. |
| 8,192,136 B2 | 6/2012 | Walter et al. |
| 8,256,332 B2 | 9/2012 | Walter |
| 8,272,225 B2 | 9/2012 | Walter |
| 8,640,585 B2 | 2/2014 | Zust et al. |
| 8,647,836 B2 | 2/2014 | Heid et al. |
| 8,687,858 B2 | 4/2014 | Walter et al. |
| 8,869,666 B2 | 10/2014 | Yang et al. |
| 8,967,024 B2 | 3/2015 | Magavi et al. |
| 8,996,570 B2 | 3/2015 | Stratman et al. |
| 9,032,854 B2 | 5/2015 | Yang et al. |
| 9,057,671 B1 | 6/2015 | Orfield et al. |
| 9,250,253 B2 | 2/2016 | Markin |
| 9,304,064 B2 | 4/2016 | Walter |
| 9,541,473 B2 | 1/2017 | Walter |
| 9,915,816 B2 | 3/2018 | Alessi |
| 10,012,567 B2 | 7/2018 | Bui et al. |
| 10,087,016 B2 | 10/2018 | Nakajima et al. |
| 10,139,613 B2 | 11/2018 | Hing et al. |
| 2002/0188224 A1 | 12/2002 | Roe |
| 2005/0126311 A1 | 6/2005 | Miyazawa |
| 2005/0235542 A1 | 10/2005 | Metzner et al. |
| 2006/0008790 A1 | 1/2006 | Hayworth et al. |
| 2007/0039435 A1 | 2/2007 | Kokubo |
| 2007/0157786 A1 | 7/2007 | Miyatani et al. |
| 2007/0180965 A1 | 8/2007 | Ito et al. |
| 2007/0199418 A1 | 8/2007 | Ito |
| 2007/0204734 A1 | 9/2007 | Ito et al. |
| 2007/0204740 A1 | 9/2007 | Miyatani et al. |
| 2008/0072723 A1 | 3/2008 | Nakajima et al. |
| 2008/0088834 A1 | 4/2008 | Miyatani et al. |
| 2008/0202308 A1 | 8/2008 | Fujiwara et al. |
| 2008/0286149 A1* | 11/2008 | Roe .................. G01N 33/48764 422/400 |
| 2009/0133556 A1 | 5/2009 | Ito et al. |
| 2009/0137028 A1 | 5/2009 | Ito et al. |
| 2009/0181422 A1 | 7/2009 | Schmitt et al. |
| 2009/0241751 A1 | 10/2009 | Walter |
| 2010/0030364 A1 | 2/2010 | Fujimoto et al. |
| 2010/0047860 A1 | 2/2010 | Fukuoka et al. |
| 2010/0050839 A1 | 3/2010 | Miyatani et al. |
| 2010/0058913 A1 | 3/2010 | Walter |
| 2010/0089516 A1 | 4/2010 | Kawamoto |
| 2010/0093022 A1 | 4/2010 | Hayworth et al. |
| 2010/0101385 A1 | 4/2010 | Walter et al. |
| 2010/0118133 A1 | 5/2010 | Walter et al. |
| 2010/0216221 A1 | 8/2010 | Walter et al. |
| 2010/0229702 A1 | 9/2010 | Fujimoto et al. |
| 2010/0279342 A1 | 11/2010 | Kijima et al. |
| 2011/0303352 A1 | 12/2011 | Nakajima et al. |
| 2012/0011975 A1 | 1/2012 | Ito et al. |
| 2013/0166072 A1 | 6/2013 | Yang et al. |
| 2014/0026683 A1 | 1/2014 | Hayworth et al. |
| 2014/0041500 A1 | 2/2014 | Isagawa et al. |
| 2014/0137715 A1 | 5/2014 | Sneyders et al. |
| 2015/0008096 A1 | 1/2015 | Ito |
| 2015/0017679 A1 | 1/2015 | Ito |
| 2015/0260619 A1 | 9/2015 | Ott et al. |
| 2015/0323925 A1 | 11/2015 | Kondo |
| 2016/0084741 A1 | 3/2016 | Bambot et al. |
| 2016/0245728 A1 | 8/2016 | Walter et al. |
| 2016/0290895 A1 | 10/2016 | Daniel et al. |
| 2017/0284904 A1 | 10/2017 | Lim et al. |
| 2017/0303832 A1* | 10/2017 | Yasui ............... G01N 33/48764 |
| 2017/0303832 A1 | 10/2017 | Yasui |
| 2017/0363519 A1 | 12/2017 | Gong et al. |

OTHER PUBLICATIONS

Woo, J. Y. Techniques for Sectioning and Staining Tissue Cultures of Western White Pine. Ogden, UT: U.S. Dept, of Agriculture, Forest Service, Intermountain Forest & Range Experiment Station, 1970. Print.

PCT/US2017/025638 Partial International Search Report dated Aug. 1, 2017.

* cited by examiner

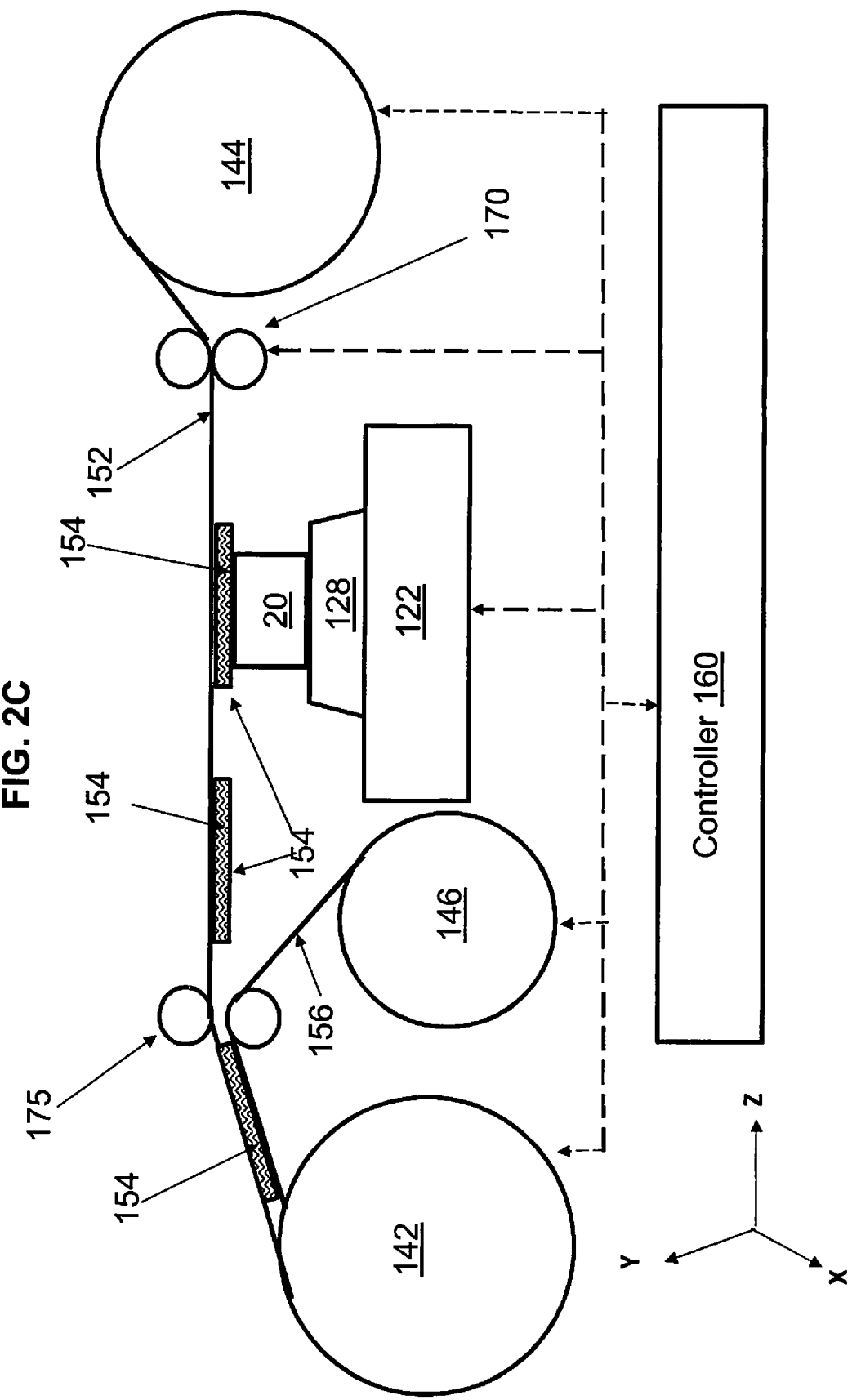

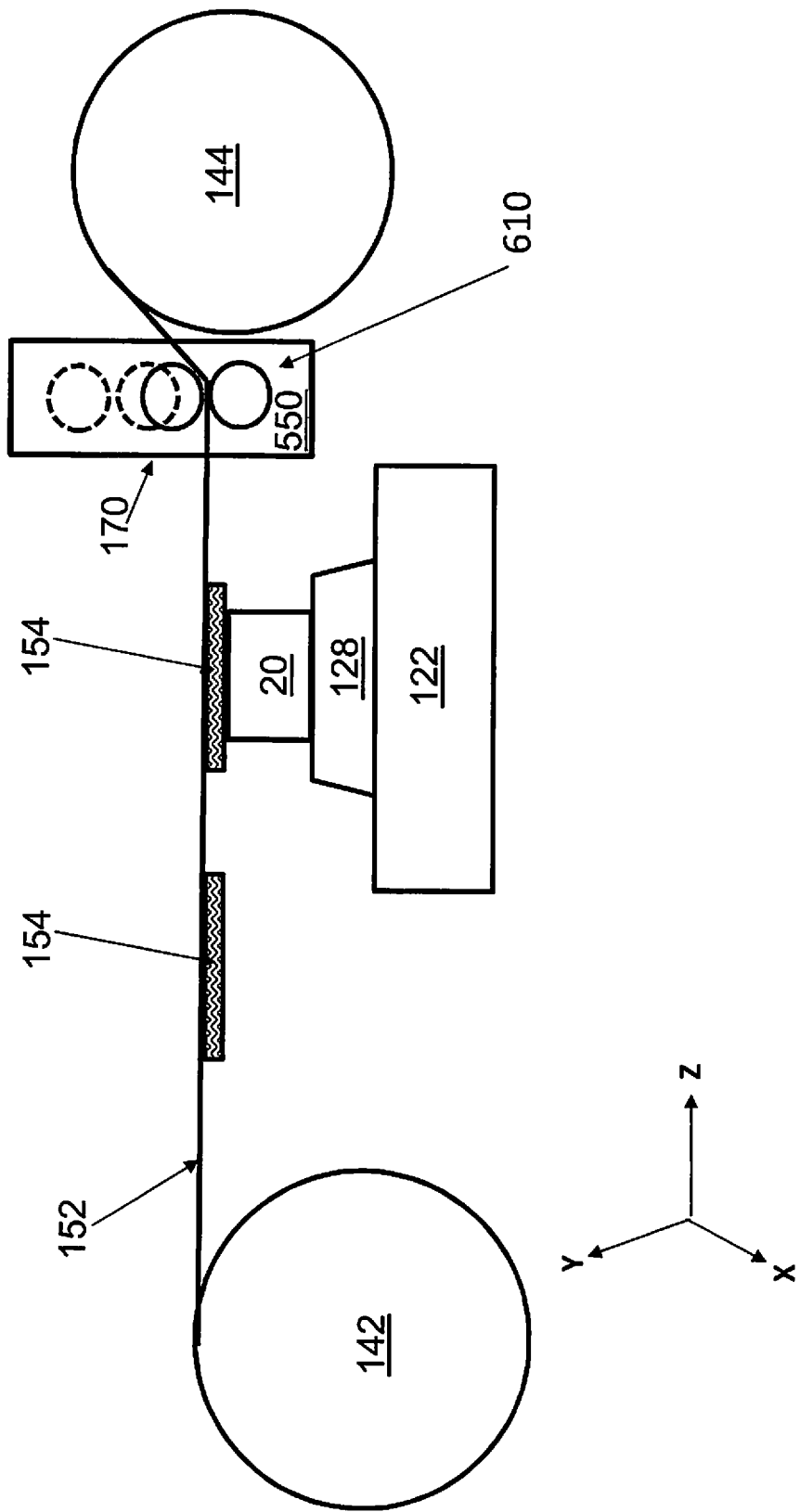

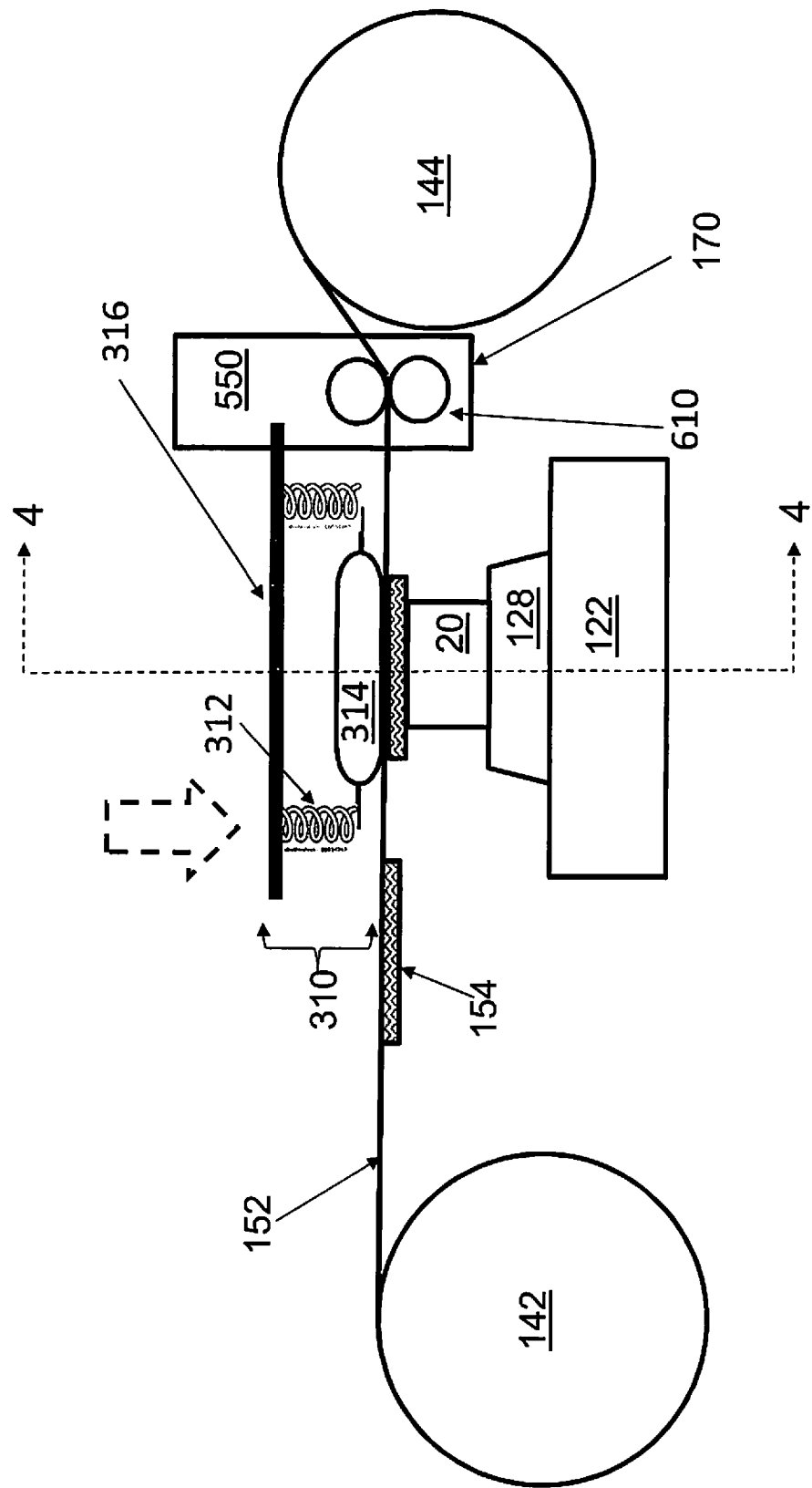

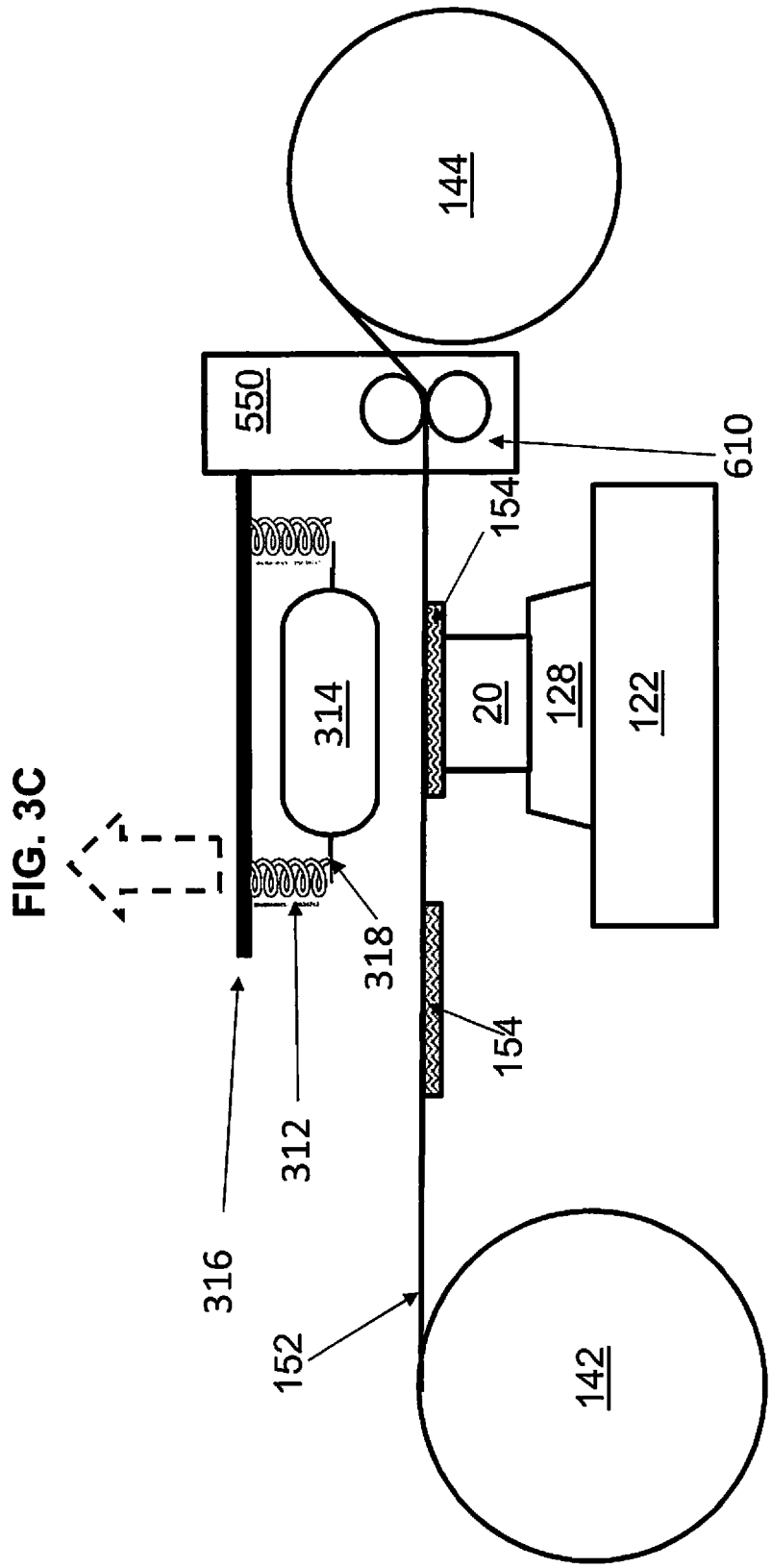

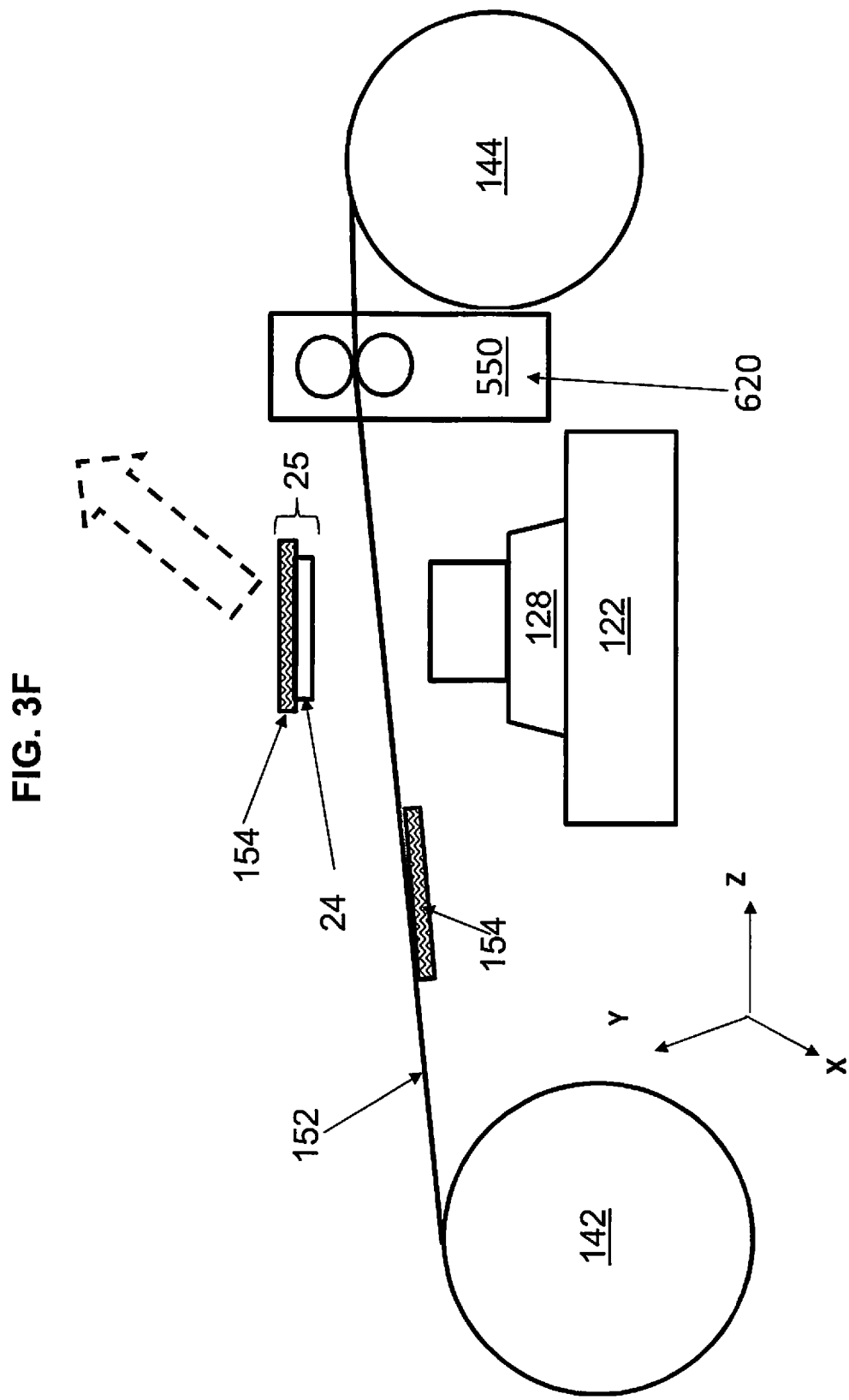

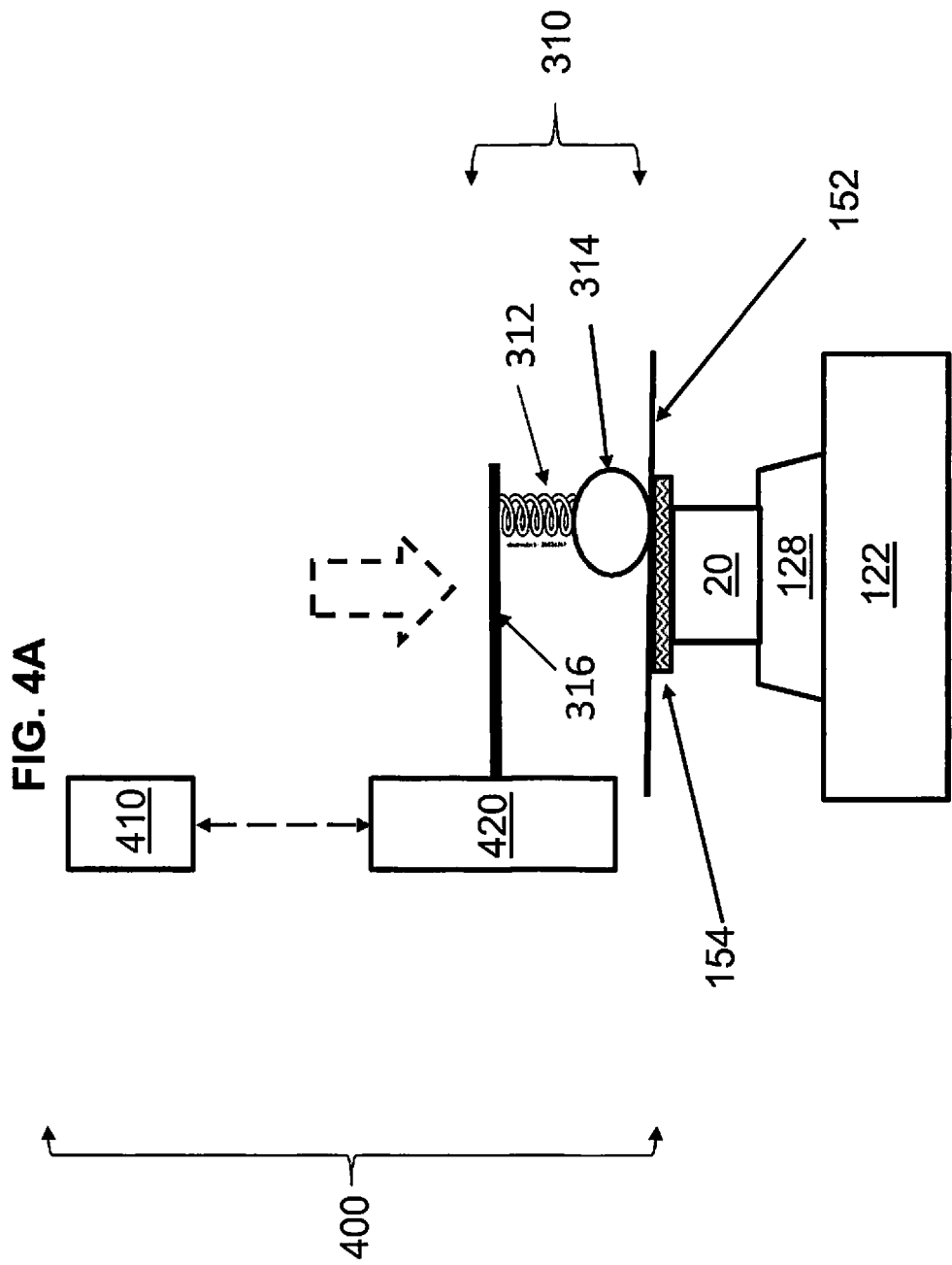

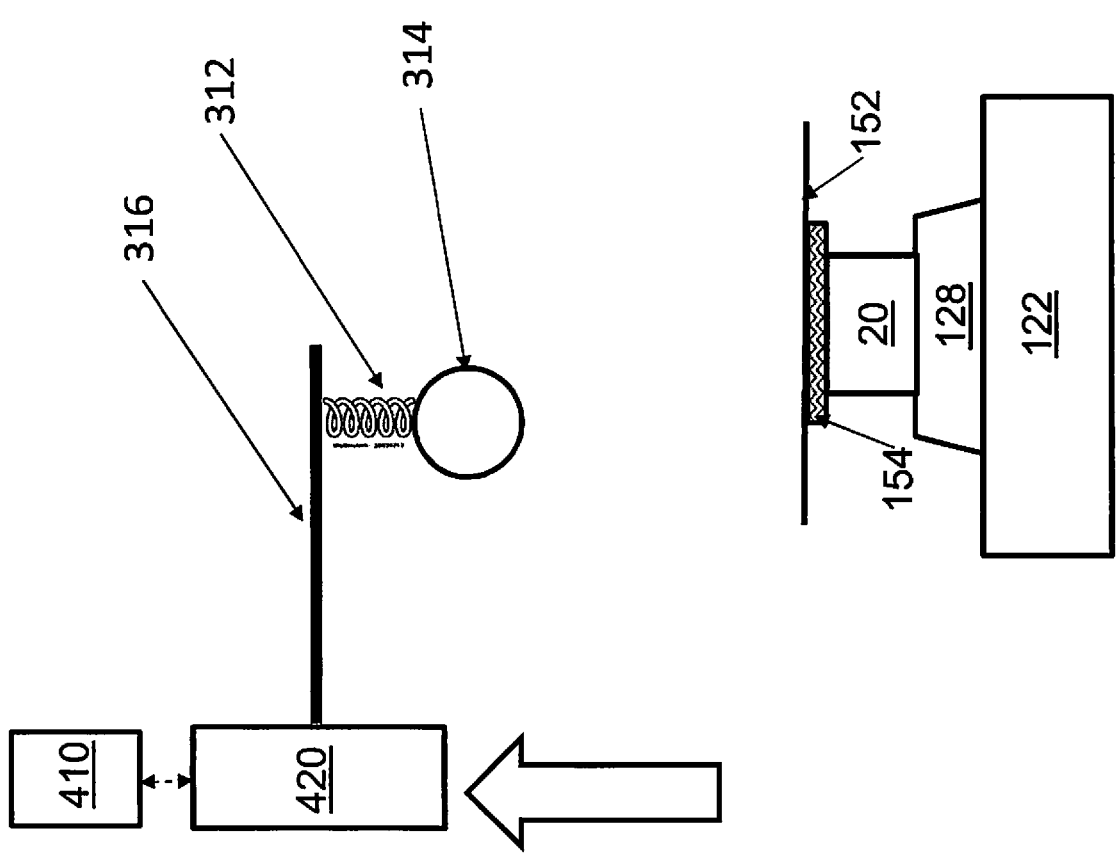

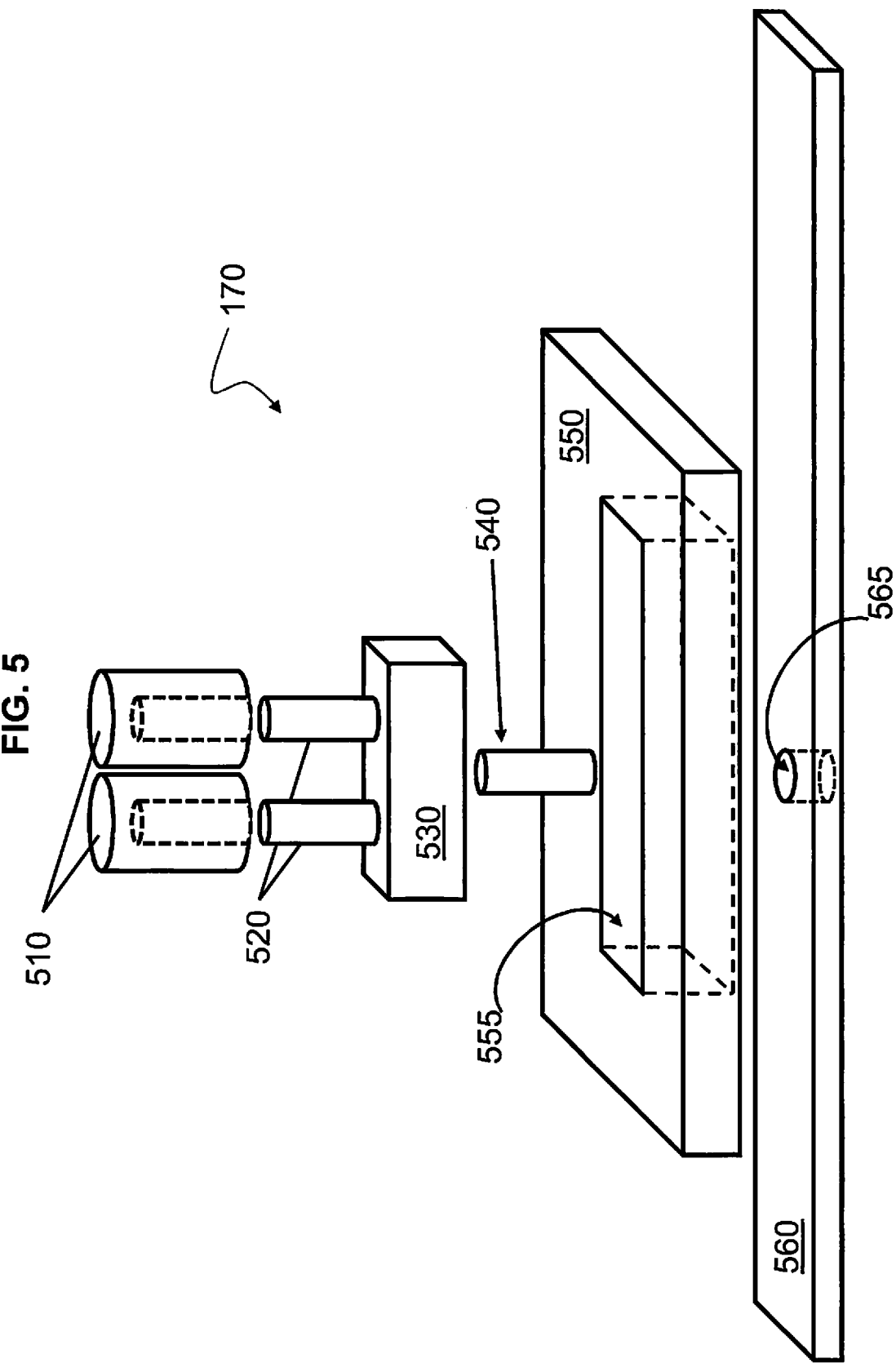

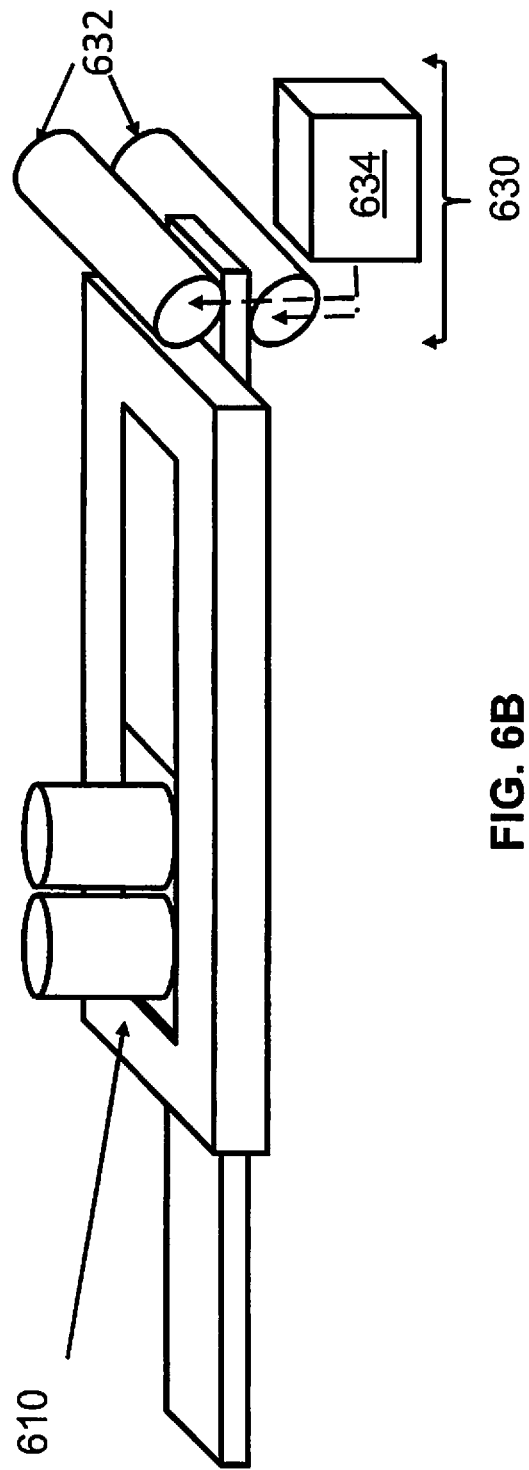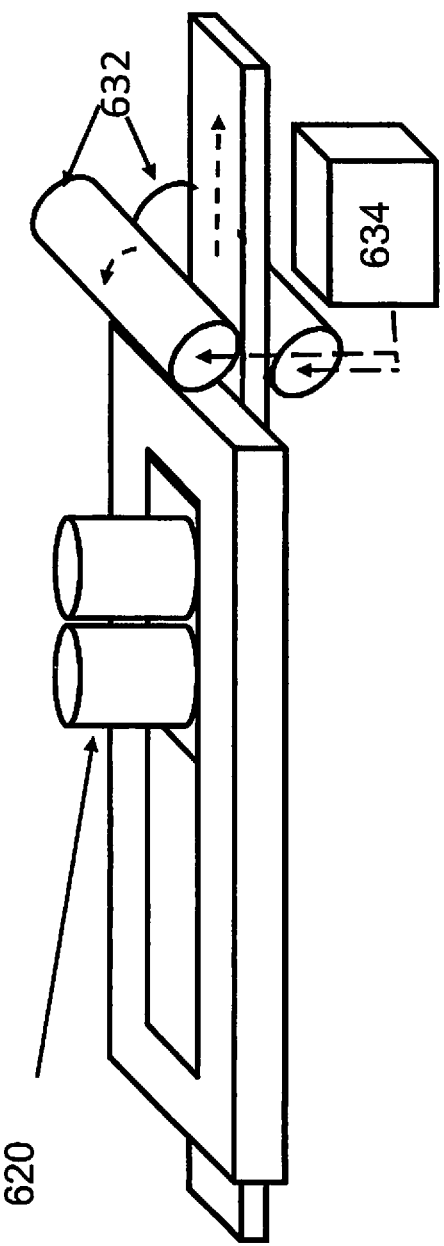
FIG. 6A
FIG. 6B

METHOD, SYSTEM, AND DEVICE FOR AUTOMATING TRANSFER OF TAPE TO MICROTOME SECTIONS

This application is a continuation of application Ser. No. 15/179,916, filed on Jun. 10, 2016, which claims priority from provisional patent application 62/187,114, filed Jun. 30, 2015. The entire contents of each of these applications are incorporated herein by reference.

FIELD

The present invention relates generally to preparing specimen sections with a microtome, and methods for sectioning materials cut from a specimen block, and more specifically to automating the sectioning process.

BACKGROUND

Microtomy is a method for preparing extremely thin sections of materials. Samples as thin as 1 to 5 micrometers (μm) can be prepared, but are more typically in the range of 10 or 20 μm to 100 μm. Historically, the purpose of preparing such thin sections has been for microscopic observation under transmitted light or electron radiation. Materials subject to microtomy can be either organic or inorganic, and typically undergo some form of advance preservation. Where the material is a biological tissue, the tissue is often preserved before sectioning, either by freezing the tissue as a tissue block, or by embedding a block of tissue in paraffin.

A microtome is the cutting instrument used to perform microtomy. Typically, microtomes include a knife blade, a cutting stage, and an apparatus on which the tissue is mounted. One such device for sectioning samples encased in paraffin is the Sakura Tissue-Tek AutoSection® Automated Microtome, which is available from Sakura Finetek USA, Inc. of Torrance, Calif.

When sectioning tissue that has been frozen, it is necessary to conduct microtomy within a chamber maintained at temperatures substantially below the freezing point of water. Certain microtomes are provided with cryogenic chambers and stages to cool and maintain the biological tissue samples at cold temperatures. Without limitation, an example of one such device is the Leica CM3050 Research Cryostat, available from Leica Microsystems Inc., of Buffalo Grove, Ill. Another model is the cryostat Microm HM550, which is available from Microm International GmbH, a division of Thermo Fisher Scientific, of Walldorf, Germany.

The CryoJane® Tape-Transfer System (developed by Instrumedics, Inc., and now available from Leica Microsystems Inc., Buffalo Grove, Ill.) is a commercially available system to facilitate the transfer of cut sections to a slide. In this procedure, adhesive tape is attached to the surface of the tissue block, or "blockface." The block is sectioned without an anti-roll plate, and the detached, cut section remains adhered to the tape without curling or other deformation. The tape and section together are placed manually onto a polymer-coated glass slide, which is cured when exposed to ultraviolet (UV) light. After curing, the tape can be removed, leaving the tissue section strongly adhered to the slide.

The normal operating mode of microtome equipment is labor intensive. All of the above-described operations are conducted manually by a human technician. One of these operations is the placement of the CryoJane® adhesive tape onto the surface of the tissue block. The adhesive tape serves to stabilize the very thin tissue sample while it is being cut, and minimizes damage to the sample during subsequent manipulations, including transport to a glass slide. Typically the tape is affixed to the sample by hand. The operator uses a roller to ensure the sample is adhered properly to the tape and to eliminate air bubbles between the tape and the sample.

The microtome's cutting blade is quite close to the mounted sample, so technicians risk personal injury. The delicate hand operations are rendered even more difficult and risky when sample preparation is performed in a cryostat environment, because the mounted sample is in close proximity to the cryogenic stage.

Moreover, the numerous manual operations in affixing the tape to the sample by hand require that the procedure be conducted in an open environment, which render samples susceptible to contamination by dust and other environmental hazards, thereby compromising sample integrity. Temperature variations inherent in an open environment also compromise sample integrity. Different types of tissue, whether they are sectioned frozen or at room temperature, have specific temperature requirements, so lab temperatures are maintained to control atmospheric instability and maintain the samples at their required temperatures. In the case of cryogenic sectioning, a lab may be maintained at temperatures colder than typical room temperatures. For example, while typical room temperatures may be 20-21° C. (69-70° F.), cryogenic sectioning may require maintaining labs at colder temperatures, for example, 18-19° C. (65-66° F.), forcing workers to perform these delicate operations in chilly conditions. Humidity variations inherent in an open environment also compromise sample integrity. Humidity is difficult to control in open environments as well. While suitable humidity levels in typical open conditions may be 22-80 proper operation of cryostat equipment and sample quality requires maintaining humidity levels at 40-60 RH %.

In addition, recent advancements in the digital imaging of tissue sample sections have made it desirable to slice blocks of specimen very quickly. By way of example, where tissues are sectioned as part of clinical care, time is an important variable in improving patient care. Every minute that can be saved during sectioning of frozen tissue for intra-operative applications of anatomic pathology, for example in examining margins of lung cancers to determine whether enough tissue has been removed, is of clinical value. To create a large number of sample sections quickly, it is desirable to automate the process of cutting tissue sections from a specimen block by a microtome blade and facilitating the transfer of cut tissue sections to an adhesive tape.

Accordingly, it is desirable to enhance operator safety and sample integrity by automating portions of the process of specimen preparation for microtome operation. Automation would allow for increased consistency, a decreased need for dedicated technician time, and less training time for technicians.

SUMMARY

In accordance with one aspect of the present disclosure, an apparatus is disclosed for sectioning a specimen block with a substantially planar exposed surface. The apparatus has a specimen holding unit for mounting the specimen with the exposed specimen surface outwardly facing therefrom and a tape transport unit for transporting one of a plurality of serially-spaced patches of sample tape along a path to a position adjacent to and covering the exposed specimen surface. The apparatus also has a tape application unit for applying the patch of sample tape to the exposed sample surface, and a specimen sectioning unit for sectioning the exposed sample surface from the sample of specimen when the patch of sample tape is adhered to the exposed sample surface.

In some embodiments, the tape application unit has a roller for pressing the patch to the exposed surface of the specimen.

In some embodiments, the apparatus further includes a cryogenic system for cooling and maintaining the specimen at cold temperatures.

In some embodiments, the tape transport unit removes the sample tape patch from the carrier strip to allow operation of the specimen sectioning unit unimpeded by the carrier strip. In some embodiments, the tape transport unit has a carrier strip take-up spool for collecting the carrier strip after removal of the sample tape patch from the carrier strip. In some embodiments, a controller is coupled to the tape transport unit that has a processor and a non-transitory computer-readable medium encoding instructions for dispensing the carrier strip so that the patch is adjacent to and covers the exposed sample surface.

In another aspect of the invention, a composite strip, for use in an apparatus for sectioning materials from a specimen having a substantially planar exposed surface, has a continuous carrier strip with a front side and a back side, and a plurality of sample tape patches serially-spaced along the carrier strip. Each patch has a carrier strip side and a sample side. In some embodiments, the patches each have an area at least as large as an area of the exposed specimen surface.

The composite strip can have a first adhesive layer between the front side of the carrier strip and the carrier strip-side of the sample tape patch. The first adhesive layer is configured to adhere the carrier strip to the plurality of patches while the composite is rolled on a spool before use and while the composite strip is unwound from the spool during and in preparation for use. The first adhesive layer can be configured to allow separation of one of the sample tape patches from the carrier strip when the sample tape patch is positioned adjacent to and adhered to the exposed sample surface.

The composite strip can also have a second adhesive layer on the sample side of the plurality of sample tape patches. The second adhesive layer is configured to minimize adhesion between the carrier strip side of the patches and the composite strip deeper within the spool before use. It is also configured to adhere the patch to the exposed specimen surface, but to allow the patch to pull off from the exposed specimen surface without damage to the exposed specimen surface after it has been sectioned from the specimen and affixed to a microscope slide.

In some embodiments, the composite strip can also have a cover strip with a front side and a back side. The cover strip may be a single continuous tape, or it may be segmental, each segment of which is spaced between two patches of sample tape on the carrier strip.

In some embodiments, the second adhesive layer is disposed between the sample side of the patches and the back side of the cover strip. In some embodiments, a first bond is formed by the first adhesive layer that is stronger than a second bond formed by the second adhesive layer.

Other embodiments include a tape transport apparatus for delivering a sample tape to an exposed surface of a specimen on a specimen holding unit having, to one flank of the specimen holding unit, a supply reel for the composite strip of the embodiments described herein. The tape transport apparatus may also have, to a second flank of the specimen holding unit, a carrier strip take-up spool for receiving the carrier strip after detachment from the sample patch; and a tape guide positioned between the specimen holding unit and the carrier strip take-up spool.

In some embodiments, the position of the tape guide in the tape transport apparatus is movable between an apply position and a remove position. In some embodiments, when the tape guide is in the apply position, an angle formed by a first line between the specimen holding unit and supply reel and a second line between the specimen holding unit and tape guide is about 180 degrees, and a sample tape segment is adjacent to and aligned with the exposed surface of the specimen. Further, when the tape guide is in the remove position, the angle formed by a first line between the specimen holding unit and supply reel and a second line between the specimen holding unit and tape guide is an obtuse angle, so as to cause separation of said carrier strip from one of the patches of sample tape adhered to the exposed specimen surface.

Other aspects of the invention include a strip tape reel for a composite strip having the features of one or more of the embodiments described herein.

In accordance with another aspect of the present invention, a method is provided for sectioning materials from a specimen having a substantially planar exposed surface. In the method, a plurality of serially-spaced patches of sample tape with an adhesive outer surface may be applied to a carrier strip. The carrier strip may be transported along a path adjacent to and spaced from the exposed sample surface to position a patch of sample tape adjacent to and covering the exposed sample surface. The patch may be adhered to the exposed sample surface removed from the carrier strip to allow sectioning of the exposed sample surface from the sample unimpeded by the presence of the carrier strip.

In some embodiments of the method, the carrier strip may be collected after its removal from the exposed specimen surface, and the path of the carrier strip may be altered in order to cause separation of the carrier strip from the patch adhered to the exposed specimen surface. In some embodiments, a computer processor and non-transitory computer-readable medium encoding instructions for transporting and positioning may be employed to control the transporting of the carrier strip and positioning of the patch adjacent to and covering the exposed sample surface.

In accordance with another aspect of the present invention, an elongated strip for use in an apparatus for sectioning materials from a specimen having an exposed surface is provided comprising a) a continuous carrier strip having a first side and a second side; b) a plurality of patches serially-spaced along the carrier strip, each of the patches including a carrier strip side and a sample side; and c) a first adherence between a first side of the carrier strip and the carrier strip side of the patches, wherein the first adherence is configured (i) to adhere the carrier strip to the patches while the elongated strip is rolled on a spool before use and while the elongated strip is unwound from the spool in preparation for use, and (ii) to allow separation of the patch from the carrier strip when the patch is positioned adjacent to and adhered to the exposed surface of the specimen.

In accordance with another aspect of the present invention, an automated tape transport apparatus for delivering a tape to an exposed surface of a specimen on a specimen holding unit is provided comprising: a) a carrier strip transport unit for transporting the tape, the tape having a carrier strip and a plurality of patches carried by the carrier strip, the patches having an adherence side for adhering to the exposed surface of the specimen for adherence of a sample sectioned from the specimen in the automated apparatus; b) a specimen holding unit for mounting the specimen with the exposed surface outwardly facing therefrom; c) a tape application unit for adhering one of the patches to the exposed surface of the specimen after transport of the patch to a position adjacent and covering the exposed surface; and d) a specimen sectioning unit for sectioning the exposed surface from the specimen when the one of the patches is adhered to the exposed surface, the patch being separable from the carrier strip.

In accordance with another aspect of the present invention, an automated tape transport apparatus for delivering a tape to an exposed surface of a specimen on a specimen holding unit is provided comprising a) a tape transport unit for transporting the tape for adhering the tape to the exposed surface of the specimen for adherence of a sample sectioned from the specimen in the automated apparatus, the tape transport unit having a supply reel and a take up reel, and the tape having a cover strip thereon; b) a specimen holding unit for mounting the specimen with the exposed specimen surface outwardly facing therefrom; c) a tape application unit for adhering the tape to the exposed surface after transport of the tape to a position adjacent and covering the exposed surface; d) a specimen sectioning unit for sectioning the exposed surface from the specimen; and e) a cover strip take up spool for taking up the cover strip when separated from the carrier strip.

In accordance with another aspect of the present invention, a tape for use in an apparatus for sectioning materials from a specimen having a substantially planar exposed surface is provided. The tape comprises a carrier strip having a first adherence having a first adherence strength, the first adherence being on a side facing the exposed surface of the specimen and providing sufficient adhesion to a sample sectioned from the specimen while allowing minimal adhesion to the carrier strip to enable unwinding of the tape from to supply spool without disturbing the adherence.

In accordance with another aspect of the present invention, an automated tape transport apparatus for delivering a sample tape to an exposed surface of a specimen on a specimen holding unit is provided comprising a) a tape transport unit for transporting a tape for adhering the sample tape to the exposed surface of the specimen for adherence of a sample sectioned from the specimen in the automated apparatus, the tape transport unit having a supply reel and a take up reel; b) a specimen holding unit for mounting the specimen with the exposed specimen surface outwardly facing therefrom; c) a tape application unit for adhering the tape to the exposed surface after transport of the tape to a position adjacent and covering the exposed surface, the tape application unit including a spring biased roller, to press the sample tape onto the exposed surface and apply a consistent pressure; and d) a specimen sectioning unit for sectioning the exposed surface from the specimen.

In accordance with another aspect of the present invention, an automated tape transport apparatus for delivering a tape to an exposed surface of a specimen on a specimen holding unit is provided comprising a) a tape transport unit for transporting a tape for adhering the sample tape to the exposed surface of the specimen for adherence of a sample sectioned from the specimen in the automated apparatus, the tape transport unit having a supply reel and a take up reel; b) a specimen holding unit for mounting the specimen with the exposed specimen surface outwardly facing therefrom; c) a tape application unit for adhering the tape to the exposed surface after transport of the tape to a position adjacent and covering the exposed surface; d) a carrier strip guide, wherein the position of the carrier strip guide is movable between an apply position for adhering the tape to the exposed sample surface and a remove position; and e) a specimen sectioning unit for sectioning the exposed surface from the specimen.

As used herein, a specimen is an organic or inorganic material that is being prepared for microscopic examination. Examples of specimens suitable for use with the invention include without limitation biological tissue, for example neurological tissue, or brain tissue.

It is to be understood that both the foregoing general description and the following detailed description are exemplary and explanatory only and are not restrictive of the invention, as claimed. Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

FIG. 2C is a partial elevated view of an alternate embodiment of the tape transport unit, in which a cover strip is provided to cover and protect patches of sample tape adhered to the carrier strip;

FIGS. 3A-3G are partial elevated views of a tape transfer and tape application system in accordance with an embodiment of the invention, during selected stages of a cycle of a microtome operation;

FIGS. 4A-4C are partial side views of a tape transfer system of FIG. 3B taken along lines 4-4 and showing operation of a sample tape application unit 400 and the sample sectioning unit 110;

FIG. 5 is an exploded perspective view of one embodiment of a carrier strip guide;

FIG. 6A is a perspective view of the carrier strip guide of FIG. 5 in an "Apply" position; and FIG. 6B is a perspective view of the carrier strip guide of FIG. 5 in a "Remove" position.

DETAILED DESCRIPTION

Reference will now be made in detail to the present exemplary embodiments, examples of which are illustrated in the accompanying drawings. Wherever possible, the same or similar reference numbers will be used throughout the drawings to refer to the same or like parts.

As noted above, a microtome is an instrument used to cut extremely thin slices of material, known as sections. Microtomes use steel, glass, or diamond blades depending upon the specimen being sliced and the desired thickness of the sections being cut. Steel blades are used to prepare sections of animal or plant tissues for light microscopy histology. Glass knives are used to slice sections for light microscopy and to slice very thin sections for electron microscopy. Industrial grade diamond knives are used to slice hard materials such as bone, teeth and plant matter for both light microscopy and for electron microscopy. Gem quality diamond knives are used for slicing thin sections for electron microscopy. Suitable microtomes useful in conjunction with the tape transfer and tape application systems of the invention include, without limitation, the Sakura Tissue-Tek Auto-Section® Automated Microtome (Sakura Finetek USA, Inc., Torrance, Calif.), the Leica CM3050 Research Cryostat (Leica Microsystems Inc., Buffalo Grove, Ill.), the cryostat Microm HM550 (Microm International GmbH, a division of Thermo Fisher Scientific, of Walldorf, Germany) and the Leica RM2125 (Leica Microsystems Inc., Buffalo Grove, Ill.).

Figure 1A:
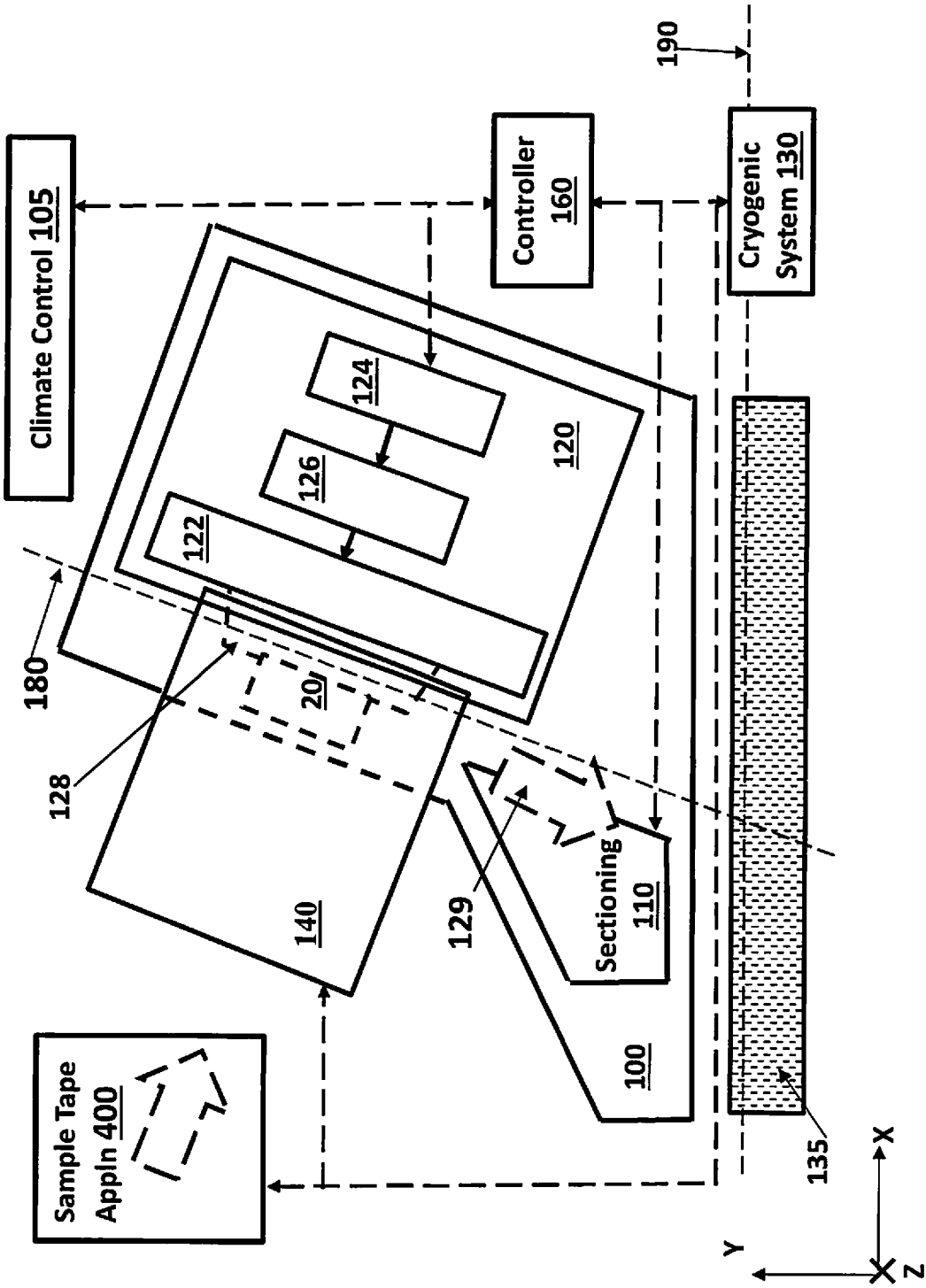
FIG. 1A is a partial schematic side view of a system of the present invention.

FIG. 1A is a partial side view of one embodiment of an improved microtome 100 system of the present invention. Certain elements of the system are shown in block form for simplicity. As shown in FIG. 1A, and with reference to FIGS. 1B, 2A, and 3E, the system for use with a microtome 100 has a sample (specimen) sectioning unit 110 having a knife-block 112 with a blade handler 114 for holding a changeable knife blade 116, an optional cryogenic system 130, and a specimen holding unit 120 with a chuck head 122 and a chuck adapter 128 for holding the sample (specimen) 20. The system for use with a microtome 100 also has an adjustment controller 124 mechanically and electrically connected to an advancement mechanism 126 for controlling the movement of the chuck head 122. The system also has a tape transport unit 140 for guiding a composite strip 150 on a path across the specimen holding unit 120 and for aligning a patch of sample tape 154 and adhering it to the sample 20. Further, although it has been noted above that it is an optional feature, the microtome 100, like the Leica CM3050 and similar microtomes can have a cryogenic system 130 for chilling and maintaining samples frozen. Cryogenic system 130 includes cryostat cold plate 135.

Figure 1B:
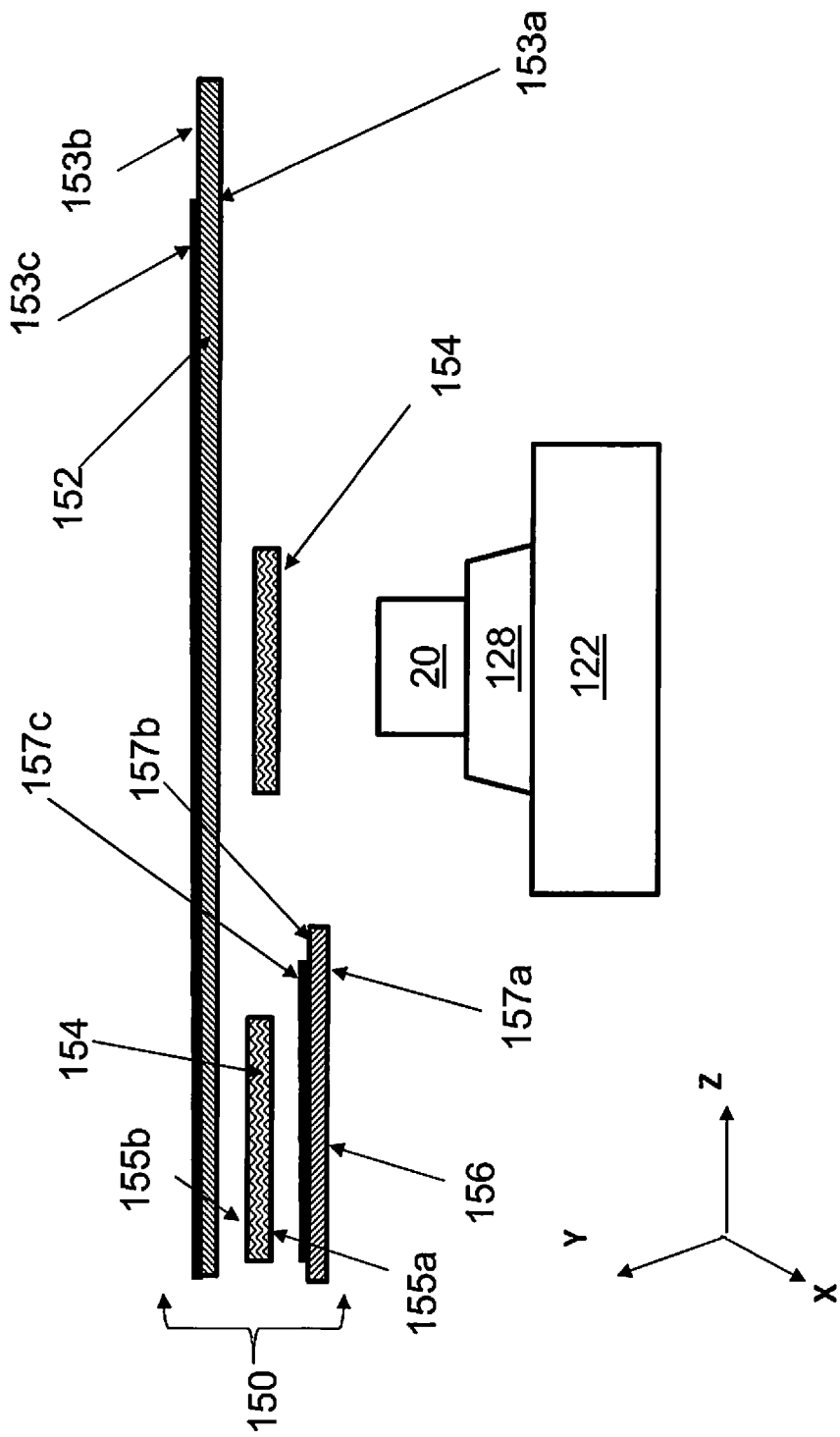
FIG. 1B is an exploded, diagrammatic representation of the relative location of elements in an embodiment of the tape transfer system during a microtome operation.
Figure 2A:
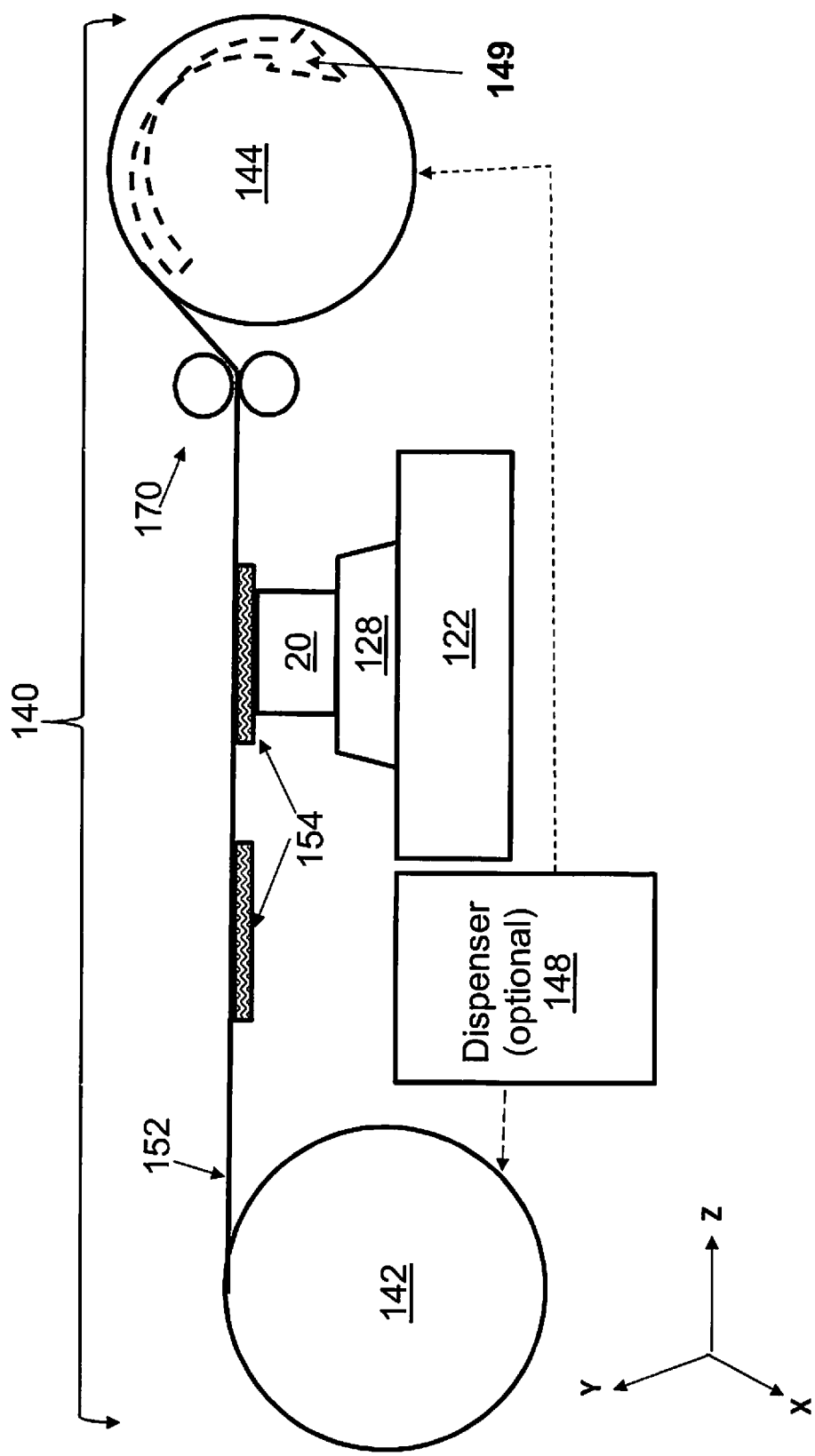
FIG. 2A is a partial elevated view of one embodiment of the tape transport unit, showing the path of the composite strip across the specimen holding unit.

Referring to FIG. 1A, the tape transport unit 140 is shown located vertically above the sample sectioning unit 110, adjacent to the sample 20 (when the sample 20 is in its highest position). FIGS. 1B and 2A show certain elements of the tape transport unit 140, which is described in more detail below with reference to FIGS. 2A-2C among other figures, part of the composite (elongated) strip 150 (a patch of sample tape 154 adhered to the sample 20 and a carrier strip 152 upon which the patch of sample tape 154 is stored (carried) until the patch is adhered to the sample 20) and a carrier strip take-up spool 144 for winding the carrier strip 152 after it has been released from the patch of sample tape 154. The path followed by the elongated strip 150 is parallel to the Z-axis. Its direction can be seen with reference to arrow 149, which shows the direction that the carrier strip 152 is wound on the carrier strip take-up spool 144.

The system for use with a microtome 100 also has a tape application system 400 for attaching a patch of sample tape 154 to the sample 20. The term sample tape 154 as used herein refers to the portions of tape, e.g., the patches of FIG. 1B, to which a sample of section cut from the sample (specimen) block adheres. Where the microtome 100 is contained within an optional closed enclosure 102 for holding and protecting the elements disclosed above, a climate-control unit 105 controls the environment in which the elements operate. Further, controller 160 controls the sample sectioning unit 110, the cryogenic system 130, specimen holding unit 120, tape transport unit 140, tape application unit 400, and climate control unit 105. In certain embodiments, the controller 160 further has a processor and a non-transitory computer-readable medium encoding instructions for controlling operation of the units and systems of the system.

As shown in FIGS. 1B and 2A, the composite elongated strip 150 is a tape having a continuous carrier strip 152 upon which are affixed serially spaced patches of sample tape 154. The carrier strip 152 has a carrier strip front side 153a facing toward the chuck adapter 128 and a carrier strip back side 153b facing away from the chuck adapter 128, and the patches of sample tape 154 have a sample tape front side 155a facing toward the chuck adapter 128 and a sample tape back side 155b facing away from the chuck adapter 128. Optionally, the composite strip 150 can further have a cover strip 156 to cover and protect the patches of sample tape 154. The cover strip 156 (which may be continuous) may have a cover strip front side 157a facing away from the patch of sample tape 154 and a cover strip back side 157b facing toward the patch of sample tape 154.

Figure 2B:
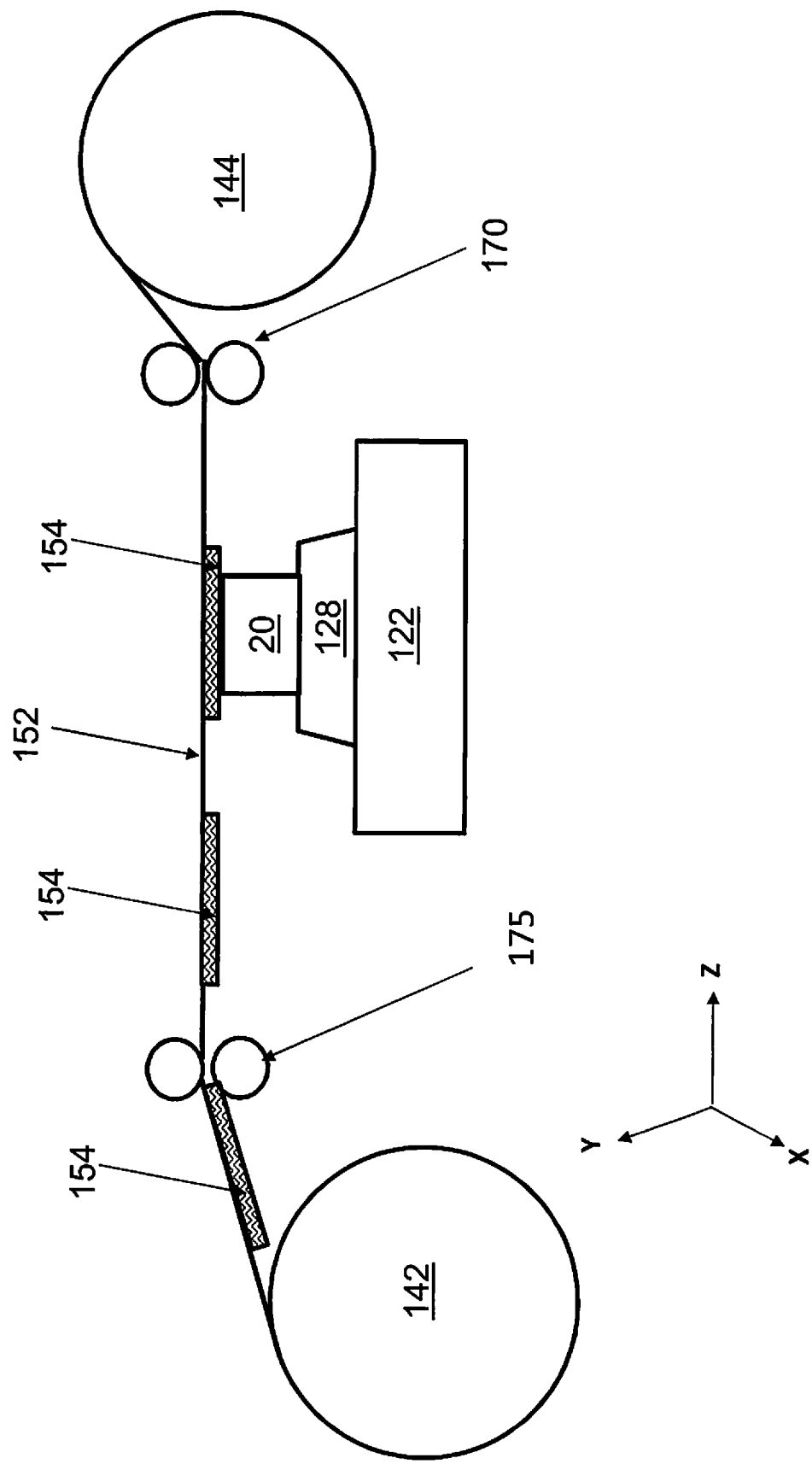
FIG. 2B is a partial elevated view of an alternate embodiment of the tape transport unit, in which a second set of tape guides is employed to guide the composite strip.

FIGS. 2A-2C are partial elevated views of embodiments of the tape transport unit 140 for guiding the composite strip 150 along a path across the sample (specimen) 20. In addition, arrow 129 (FIG. 1A) shows the direction of the motion of the sample 20 during cutting, the path of the composite strip 150 being in a plane substantially perpendicular to the direction of motion of the sample 20 during cutting.

FIG. 2A shows a tape transport unit 140 with a supply spool 142 and a carrier take-up spool 144 for transporting a composite strip 150 along a path adjacent to and spaced from the exposed surface of the sample 20 on the chuck adapter 128. The composite strip 150 may be held taut between spools 142, 144 by any conventional method, such as those methods well known in the art of reel-to-reel tape recorders. The tape transport unit 140 has a suitable guide system for guiding the movement of the composite strip 150 from supply spool 142 to the carrier take-up spool 144. One such guide system is shown in FIG. 2A, in which the tape transport unit 140 has carrier strip guide 170, described in further detail below.

FIG. 2B is a partial elevated view of a second embodiment of the tape transport unit 140, in which a second set of guides, the supply spool carrier strip guide 175, is employed to guide the composite strip 150. FIG. 2C is a partial elevated view of a third embodiment of the tape transport unit 140 of the microtome 100 for guiding the path of the composite strip 150 when it employs the cover strip 156 shown in FIG. 1B. The cover strip 156 is provided to cover the composite strip 150 and protect patches of sample tape 154 adhered to the composite strip 150.

The cover strip 156 may be continuous, or it may be segmental (as discrete patches, by being serrated, or by periodically having decreased width), with each segment of the cover strip 156 spaced between two patches of the sample tape 154 on the carrier strip 156. As shown in FIG. 2C, the tape transport unit 140 may have a cover strip take up spool 146 to collect the cover strip 156 once it is separated from the sample tape 154. Where the cover strip is segmental, the cover strip does not cover the sample tape but rather is in between the patches. After the patch of sample tape 154 is removed from the carrier strip by applying it to the specimen surface, the carrier belt is wound onto the take up spool 144 with the cover segments still attached. The cover segments would wind into the take-up spool along with the carrier strip.

Optionally, where carrier strip 152 is provided without pre-assembly with sample tape, the tape transport unit 140 also has a motorized dispensing unit, also known as dispenser 148, coupled to the spools 142, 144. In one non-limiting configuration, the optional dispenser 148 may be located above the blade handler 114 (See FIG. 3E) at the highest position of the chuck head 122. In one non-limiting embodiment, dispenser 148 is fitted to use the tape dimensions of sample tapes supplied by Leica Microsystems Inc. (CryoJane® Tape-Transfer, Leica Microsystems Inc., Buffalo Grove, Ill.). Dispenser 148 can be adjusted for tape length and width in order to accommodate different sample dimensions.

The controller 160 is coupled to the dispenser 148 and the carrier strip guide 170 for controlling the movement of the composite strip 150 from the supply spool 142 to the carrier take-up spool 144, controlling alignment of the composite strip 150 with the sample 20, and, as described in more detail below, for controlling the movement of the carrier strip guide 170 to alter the path of composite strip 150 relative to the spools 142, 144.

An adhesive layer or coating is a property at the interface between two surfaces which confers an adherence, e.g., a stickiness or clinginess, between two surfaces. Preferably the adhesive layer property is conferred by a chemical adhesive which binds or sticks the two sides or surfaces together. Alternatively, the adhesive layer property is a property which confers attractive adherence between two surfaces, which can be, e.g., static or the property associated with adherence of a film to a surface. Thus, any of these methods or processes provides an adherence between the surfaces.

Returning to FIG. 1B, the tape back side 155b of the patch of sample tape 154 has an adherence in the form of an adhesive coating selected to allow the sample tape back side 155b to adhere to the carrier strip front side 153a while the patches of sample tape 154 are rolled with the carrier strip 152 onto the supply spool 142 before use. The adhesive coating so applied is selected to allow adhesion between the sides 155b and 153a while the composite strip 150 is unwound from the supply spool 142, but also to allow separation of the patches of sample tape 154 from the carrier strip 152 after a patch of sample tape 154 is adhered to the sample 20. The adhesive coating on tape back side 155b can be, e.g., an acrylic adhesive (available from, e.g., the 3M Company of St. Paul, Minn.).

In other embodiments, the adhesive property creating the adherence is conferred by a polyester film to cover and then peel from the sample 20. An uncoated polyester liner such as those employed on new computer or cellphone screens may be employed. Suitable films include the Silicone release liner 4986 or 3M Non-Silicone Secondary Release Liner 4935, which is available from The 3M Company (St. Paul, Minn.).

In addition, the front side 155a of the patch of sample tape 154 has another adherence in the form of an adhesive coating selected to allow the patch of sample tape 154 to adhere firmly enough to the sample 20 to maintain the sample's integrity, but to pull off the sample 20 without damage to the sample 20 after the sample 20 has been affixed to a microscope slide. One exemplary adhesive coating for application to the sample tape front side 155a is the 3M silicone adhesive or silicone/rubber blend as found on 3M 1280 Tape or 3M Polyester Tape 8911 available from The 3M Company of St. Paul, Minn., and Scapa 571 Silicone Splicing Tape (also featuring silicone adhesive on a polyester backing), which is available from SCAPA North America of Windsor, Conn. Another exemplary adhesive coating for application to the sample tape front side 155a is the adhesive used on the specimen-side of the tape supplied as part of the CryoJane® system (Leica, Microsystems, Inc., Buffalo Grove, Ill.).

The type of adhesive suitable for application to the sample tape front side 155a will vary, depending on the kind of sample to be sectioned. For example, a suitable adhesive for adhering the patch of sample tape 154 to a frozen sample would not be equally effective when used to apply a patch of sample tape 154 to a sample encased in paraffin. Where the sample is embedded in paraffin, it is preferable to use the higher strength polyimide/silicone mixes.

Further, recognizing that the sample tape 154 is rolled onto the supply spool 142 before use, in embodiments not employing a cover strip 156 to protect the patch of sample tape 154 (such as shown in FIGS. 2A and 2B), the adherence provided can be an adhesive coating on the patch of sample tape front side 155a selected to also allow sufficient adhesion between the patch of sample tape 154 and the sample 20 while allowing minimal adhesion between the patch of sample tape front side 155a and carrier strip 152 deeper within the supply spool 142 so that the roll of composite strip 150 may be unwound from the supply spool 142 without disturbing the bond between sides 153a, 155b.

Alternatively, minimal adherence, e.g., adhesion, between sides 153b and 155a may be secured by applying a release coating 153c to the carrier strip back side 153b or using a carrier strip with a release coating 153c to ensure easy removal of the sample tape front side 155a therefrom. Suitable material for the carrier strip 152 include a low tack release liner, such as the 3M Silicone Release Liner 4986, the 3M Secondary Release Liner 7526L, and a Low Tack Paper Tape 3051, all of which are available from The 3M Company of St. Paul, Minn.

In the embodiment shown in FIGS. 1B and 2C, in which a cover strip 156 is used to protect sample tape patches 154, the adherence provided can be an adhesive layer on the patch of sample tape front side 155a selected to also allow minimal adhesion between the patches' sample tape front side 155a and cover strip back side 157b. Alternatively, minimal adherence, e.g., adhesion, between sides 157b and 155a may be secured by employing a release liner for the cover strip 156, or by applying a release coating 157c to the cover strip back side 153b to ensure easy removal of a patch of sample tape front side 155a therefrom. Suitable material for the cover strip 156 include a low tack release liner, such as the 3M Silicone Release Liner 4986, the 3M Secondary Release Liner 7526L, and a Low Tack Paper Tape 3051, all of which are available from The 3M Company of St. Paul, Minn.

Referring to FIG. 2A, the tape transport unit 140 is coupled to the controller 160 for automatically moving the composite strip 150 from supply spool 142 to the carrier take-up spool 144, for controlling alignment with the sample 20, and for moving the composite strip 150 relative to the spools 142, 144. The controller 160 is coupled to the spools 142, 144, for automatically transporting the composite strip 150 forward a selected amount such that the composite strip 150 is aligned with the specimen 20. The tape transport unit 140 also has a carrier strip guide 170 to which the controller 160 is coupled for guiding the composite strip 150 and for moving it relative to the spools 142, 144.

As shown in FIG. 2B, the tape transport unit 140 may also have a supply spool carrier strip guide 175 to keep the composite strip 150 in the proper position as the composite strip 150 exits the supply spool 142 and to position the composite strip 150 parallel to and a small distance from the exposed sample surface as the composite strip 150 travels toward the sample 20. In one embodiment, the supply spool carrier strip guide 175 is a pair of polished guide wheel cylinders between which the composite strip 150 may move with minimum friction, while holding the composite strip 150 substantially parallel to and a small distance from the surface of the sample 20. In one embodiment, the supply spool carrier strip guide 175 may be fixed relative to the supply spool 142 so as to contribute passive guidance of the composite strip 150 as it exits the supply spool 142 and as described below to the separation of the sample tape 154 from the carrier strip 152. In another embodiment, as shown in FIG. 2C, the supply spool carrier strip guide 175 may be positioned with the cover take-up spool 146 to effect the separation of the cover strip 156 from the carrier strip 152 and sample tapes 154 by directing the cover strip 156 along a tape path that is different from the one taken by the carrier strip 152.

The strip guides 170 and 175 ensure that the carrier strip 152 is correctly positioned so that the affixed patches of sample tape 154 may be applied to the sample 20. Subsequently the carrier strip guide 170 pulls the carrier strip 152 away from the sample tape 154, allowing microtome cutting to proceed unimpeded by the carrier strip.

One embodiment of a tape transport mechanism with a movable carrier strip guide 170 is shown in FIG. 5, with guide wheels 510, guide wheel posts 520, a movable block 530 into which fits a control rod pin 540, a stationary slotted block 550, and a movable control rod 560. The guide wheels 510 may be two polished guide wheel cylinders between which the carrier strip 152 may move with minimum friction, while holding the carrier strip 152 at least one of its potential positions: a first position (herein referred to as the "Apply" position 610 in FIGS. 3A-3C) for holding the carrier strip 20 substantially parallel to and a small distance from the surface of the sample 20, and a second position (herein referred to as the "Remove" position 620 in FIG. 3D) for changing the angle of the composite strip 150 relative to the sample 20 and thus causing a separation between the carrier strip 152 and the sample tape 154.

The guide wheel posts 520 may be two matching posts polished to mate snugly, but with minimum rotational friction, to the guide wheels 510. The guide wheel posts 520 may be attached on one side of the movable block 530, and one end of the control rod pin 540 may be attached to the opposite side of the movable block 530. The movable block 530 may fit snugly, but with minimum sliding friction, into a block slot 555 in the stationary slotted block 550, and the other end of the control rod pin 540 may be attached to the movable control rod 560 through an aperture 565 in the movable control rod 560. When assembled, the carrier strip guide 170 may assume at least one position, such as an "Apply" position 610 and a "Remove" position 620, according to the motion of the movable control rod 560. The carrier strip guide 170 in the "Apply" position 610 is shown in FIG. 6A, and the carrier strip guide 170 in the "Remove" position 620 is shown in FIG. 6B. The movable control rod 560 is actuated by, e.g., an actuator system such as an electric motor or stepper motor inside the enclosure of the microtome 100, a hydraulic or pneumatic piston inside the enclosure, or a mechanical lever system that penetrates the enclosure wall and is actuated manually or by other means from outside the instrument. One suitable actuator system is a control rod actuator system 630 having a set of rollers 632 mechanically coupled to a motor 634. The rollers 632 may be two cylinders formed of, e.g., rubber, and pressed against opposite sides of the movable control rod 560.

In operation of this embodiment, the motor 634 causes the rollers 632 to press and roll against opposite surfaces of the control rod 560. The rolling action causes control rod 560, and the movable block 530 connected thereto, to move along the block slot 555 of the stationary block 530, which causes the guide wheels 510, connected to the movable block 53, to move between the "Apply" position 610 and the "Remove" position 620. The carrier strip guide 170 may be implemented in a variety of ways. For example, in other embodiments of the carrier strip guide 170, the rotational friction of the guide wheels may be reduced by providing low-friction bearing surfaces between the guide wheels 510 and the guide wheel posts 520, or by mounting the guide wheel posts 520 in the movable block 530 with bearings (not shown). Suitable bearings may be simple polished surfaces of hard non-corroding materials, or roller bearings, or ball bearings. Many such bearing types are familiar to those skilled in the mechanical arts.

Figure 3D:
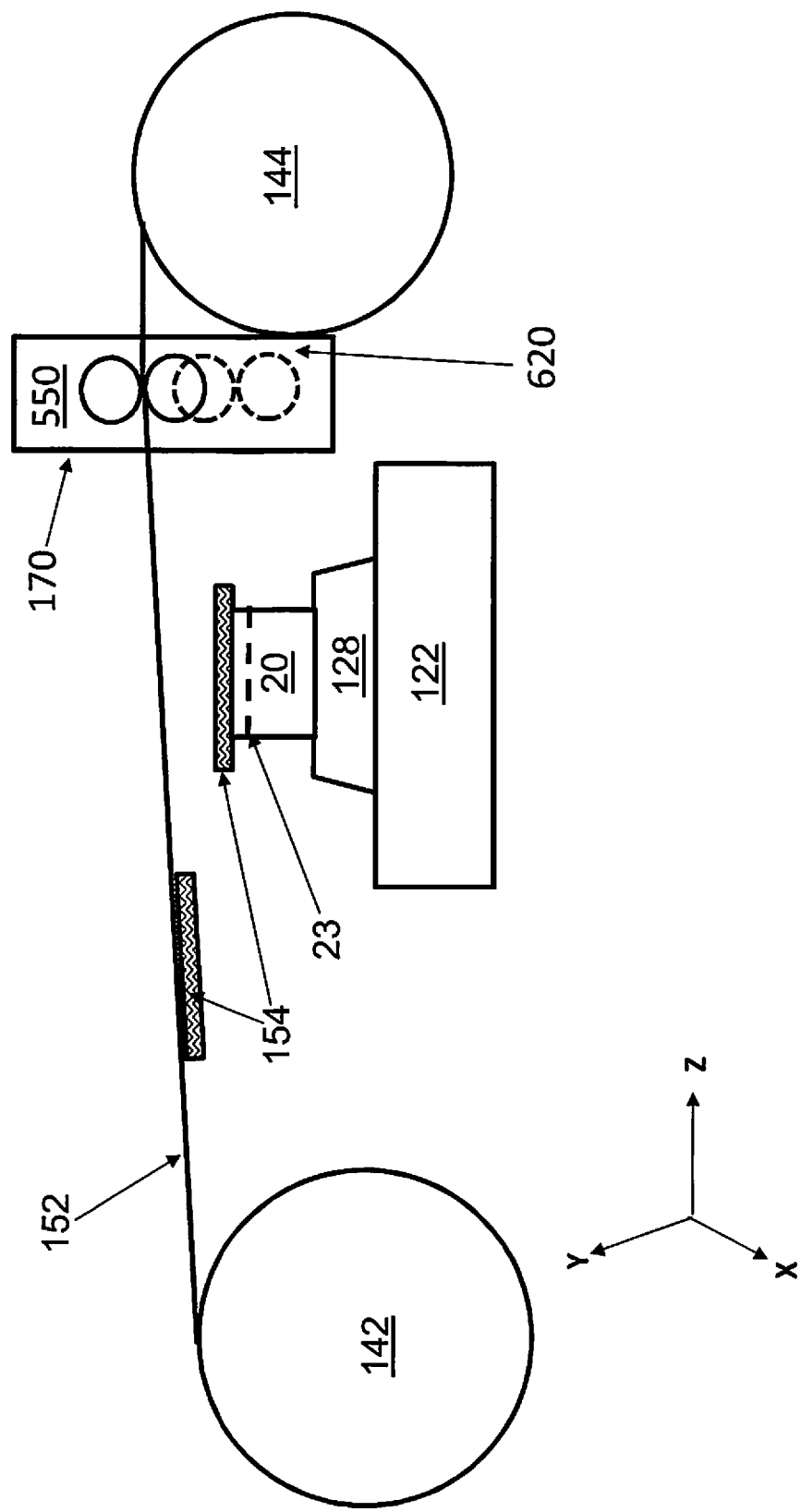
Figure 4B:
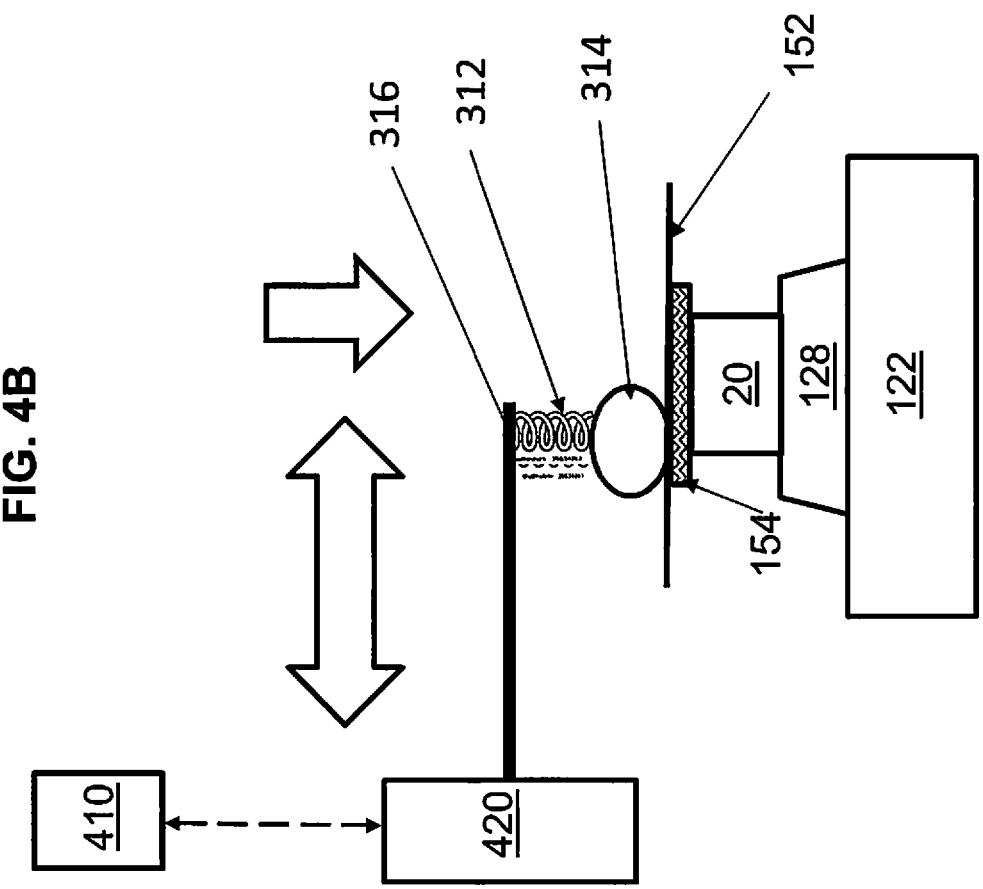

As seen in FIGS. 1A and 4A-4C, a sample tape application unit 400 applies the patch of sample tape 154 to the surface of the sample 20. The sample tape application unit 400, seen in FIG. 4A with reference to FIGS. 3B and 3C, may have a servo-sensing mechanism for sensing the location of the sample tape 154 relative to the sample 20 and the tape application elements, which are described in more detail below, and controlling the movement of the application elements toward, across, and away from the sample 20. Conventional, known pressure-sensing servo mechanisms may be used to control the application of the sample tape to the surface of the sample 20. In addition, adaptive controlled sensor/actuators may be provided to provide height control of the sample tape application process. One suitable cost-effective embodiment of a servo-sensing mechanism for the sample tape application unit 400 is shown in FIGS. 4A-4C with reference to FIGS. 3B and 3C. In the shown embodiment, the sample tape application unit 400 has a sensor 410, shown in block form in FIGS. 4A-4C, which is electronically coupled to a reciprocating actuator 420, also shown in block form. The sensor 410, which may be a light sensor or other conventional or well-known sensing device, is arranged to sense the location of the sample tape 154, the sample 20, and the spring-loaded roller assembly 310 relative to each other. The sensor 410 is arranged to provide desired locational information to the reciprocating actuator 420, and to obtain from the reciprocating actuator 420 additional desired locational information. Together, the sensor 410 and reciprocating actuator 420 may operate to align the spring-loaded roller assembly 310 and the chuck head 122.

FIGS. 4A-4C are partial side views of the tape application system of FIG. 3B taken along lines 4-4 and showing the spring-loaded roller assembly 310 mounted on the reciprocating actuator 420. The precise placement of the reciprocating actuator 420 relative to the spring-loaded roller assembly 310 is not critical, because, optionally, reciprocating actuator 420 may also be connected to the roller assembly with articulated arms (not shown).

The spring-loaded roller assembly 310 may have a set of springs 312 connecting a roller 314 and a bar 316, which in turn may be connected to the reciprocating actuator 420. In some embodiments, the roller assembly is spring biased toward the specimen holding unit. In certain embodiments, the spring-loaded roller assembly 310 may be arranged to move from one side to the other side of the sample surface. In other embodiments, the spring-loaded roller assembly 310 may be arranged to move from the top to the bottom, or from the bottom to the top, of the sample surface. In either case, the roller movement is arranged to ensure that the tape is pressed into the sample surface and that the spring-loaded roller assembly 310 does not interfere with the other tape wheels, such as spools 142, 144. Also, in either case, the spring-loaded roller assembly 310 is arranged to retract from the sample surface. Once the spring-loaded roller assembly 310 retracts, the chuck head 122 is arranged to revert to its start position (at the top of its movement).

Reference may now be had to FIGS. 3A-4C to illustrate the process of automating transfer of a sample tape 154 to a specimen segment 24. Certain elements, such as the supply spool carrier strip guide 175, have been eliminated from FIGS. 3A-4C, and other elements, such as controllers, the sensor 410 and reciprocating actuator 420, have been represented in block forms in order to simplify the drawings to better illustrate the stages of the disclosed process. While the illustrations do not show elements shown in some of the other figures or they show them in simplified form, it is to be understood that the process is not limited to operate on only those elements shown, and it will operate equally well in other environments.

The sequence of operations shown in FIGS. 3A-3E, with reference to FIGS. 4A-4C, positions the sample tape in front of the sample of the sample block, causes the patch of sample tape 154 to adhere to the sample 20, peels the carrier strip 152 off the patch of sample tape 154, sections the sample 20 from the sample block, also referred to as the cut section, moves the sample/sample tape combination (also known as the tape-specimen segment 25) away from the sectioning site, and advances the carrier strip 152, ready to start the cycle again for application of the next patch of sample tape to the sample block.

The process starts as shown in FIG. 3A, when the chuck head 122 has advanced to a microtome-ready position, with the sample 20 advanced to a position ready for cutting and a patch of sample tape 154, carried on the carrier strip 152, aligned above the sample 20. A motorized dispensing unit 148 (also known as dispenser 148) controlled by the controller 160, outputs the composite strip 150 from the supply spool 142 so that one patch of sample tape 154 is disposed parallel to and facing the surface of sample 20. As shown in FIG. 3A, the carrier strip guide 170 is in the "Apply" position so that the carrier strip 152, upon which is adhered the patch of sample tape 154, may be substantially parallel to the surface of the sample 20 to be cut by the microtome, and positioned a distance from it substantially equal to the incremental distance of advance of the chuck head 122, i.e., the thickness of the intended microtome slice. The "Apply" position is accomplished by operation of the moveable carrier strip guide 170, which may be moved as described above to hold the carrier strip 152 in a position substantially parallel to and a small distance from the surface of the sample 20.

As shown in FIGS. 3B and 3C, the tape application process may operate to apply the patch of sample tape 154 to the surface of sample 20. The patch is moved in a substantially perpendicular motion to the exposed surface of the specimen. The sample tape 154, which at this time is still applied to the carrier strip 152, adheres to the surface of the sample 20 by any suitable operation that allows for uniform tape placement, without creases, bends, or air bubbles, such as by a combination of a soft-vacuum pump or a clip mechanism. Note in some embodiments, the tape is applied from the edge of the block face to the opposite edge to avoid trapping air bubbles under the tape. FIG. 3B shows one embodiment of a tape application process moving the spring-loaded roller assembly 310 into position above the sample 20 in a substantially perpendicular position in the illustrated embodiment, and physically pressing the carrier strip 152 onto the sample 20 to adhere the sample tape 154, which is disposed between the carrier strip 152 and the sample 20, gently onto the block of tissue.

In the embodiment shown in FIGS. 3A-3G and 4A-4C, the reciprocating actuator 420 is located above the sample sectioning unit 110, with a movement mechanism that allows it to move parallel to the chuck head 122. This could be done by combining stepper motors moving along two orthogonal axes x and y, with the x and y motions coupled in order to produce an angular motion. Roller 314 is prevented from dropping by stiffness of the springs. Alternatively, if necessary, the roller 314 may be fixed to a holder (not shown) that moves it so that it does not drop down with gravity. The roller arm 318, shown in FIG. 3C, which holds the roller 314, may be flexible (e.g., a thin metal strip) to provide additional "spring".

In this embodiment, the reciprocating actuator 420, in association with the sensor 410, causes the bar 316 to move a selected amount in as many dimensions as is necessary to align the roller 314 with the carrier strip 152 and the patch of the sample tape 154 over the sample 20, and to contact the carrier strip back side 153b. The motion of the roller 314 is predetermined because the location of the sample tape 154 is known to be in a line between carrier strip guide 170 and supply spool carrier strip guide 175, so that it is always returned to the same position. Alternatively, for a more elaborate system, the sensor 410 may sense the location of the sample tape 154, the sample 20, and the spring-loaded roller assembly 310 relative to each other, provides locational information to the reciprocating actuator 420, and obtains from the reciprocating actuator 420 additional desired locational information. Together, the sensor 410 and reciprocating actuator 420 operate to align the spring-loaded roller assembly 310 and the chuck head 122.

The reciprocating actuator 420 then may cause the bar 316 to compress the springs 314 with a predetermined force sufficient to provide a soft, active pressing of the roller 314 to adhere the tape to the exposed sample surface. The roller 314 may deform slightly on the surface of the carrier strip back side 153b. The roller 314, which may be formed of a material such as a hard rubber, plastic, polyethylene, or polyvinyl chloride (PVC), rolls the sample tape 154 smooth on the surface of the sample 20, eliminating air bubbles and ensuring a firm, consistent adhesion between the surface of the sample 20 and the sample tape front side 155a. The predetermined force provided by the springs 314 (typically the same or substantially similar as that used by a human operator) ensures a consistent pressure on the carrier strip 152 to effect smoothing the patch of sample tape 154 on the sample 20.

In one embodiment, as shown in FIG. 4A, the actuator 420, through movement of the bar 316, advances the roller 314 toward the sample 20 in order to contact the carrier strip back side 153b. As shown in FIGS. 3B and 4B, the actuator 420 applies force to the roller 314 to run the roller 314 across the carrier strip back side 153b. The springs 312 act to modulate the force between the roller 314 and the composite strip 150 while giving a selected amount of flexibility to the positioning of the roller 314 against the composite strip 150. The springs 314 may be stiff compared to the weight of the roller 316 so that the combination stays aligned to the sample 20 if the reciprocating actuator 420 is not providing pressure against the sample.

As shown in FIGS. 3C and 4C, the tape application process may operate to move the spring-loaded roller assembly away from the sectioning site when the patch of sample tape 154 is adhered to the surface of sample 20. With input from the sensor 410, the reciprocating actuator 420 and spring-loaded roller assembly 310 retract and return to the initial position away from the sample 20, to which is now adhered the sample tape 154. In certain embodiments, the spring-loaded roller assembly 310 may approach the chuck head 122 from either the side or the front of the chuck head 122. Where the roller 314 moves in an up to down motion relative to the chuck head 122, the roller 314 may then retract. Where the roller has a side to side motion, it is arranged to not interfere with the carrier strip guides 170 and optional supply spool carrier strip guides 175.

FIG. 3D shows a stage of the tape application process in which the carrier strip 152 is separated from the sample tape 154 and prepares to section the sample 20 at dotted line 23. As shown in FIG. 3D, the carrier strip guide 170 moves from the "Apply" position 610 to the "Remove" position 620, thus changing the angle of the composite strip 150 relative to the sample 20. In the "Apply" position 610, the carrier strip 152 is parallel to the sample 20. The movement of the carrier strip guide 170, within the stationary slotted block 550 away from the sample 20 to the "Remove" position 620 forces the composite strip 150, which includes both the carrier strip 152 and the patch of sample tape 154, out of its path parallel to the surface of the sample 20 and into a new path that is disposed at an angle from the sample 20. The angular disposition of carrier strip 152 relative to surface 20 while the patch of sample tape 154 is firmly adhered to both the sample 20 and the carrier strip 152 causes strains to be imposed on the adhesions between the carrier strip 152 and the patch of sample tape 154. It also causes strains to be imposed on the adhesions between the patch of sample tape 154 and the sample 20. As described above, the patch of sample tape 154 may have adhesives on both of its sides 155a, 155b. The adhesive on the sample tape front side 155a (facing the surface of the sample 20) and the adhesive on the sample tape back side 155b (facing the carrier strip 152) is selected so that the amount of stress required to fracture the adhesion between the patch of sample tape 154 and the sample 20 is greater than the amount of stress required to fracture the adhesion between the patch of sample tape 154 and the carrier strip 152. Therefore, the stresses imposed by the angular disposition of carrier strip 152 relative to the sample 20 while the sample tape 154 is firmly adhered to the sample 20 causes the adhesion between the carrier strip 152 and sample tape 154 to give way, resulting in a separation of the patch of sample tape 154 from the carrier strip 152.

In embodiments having no supply spool carrier strip guide 175, the vertex of the angle of disposition of the composite strip 150 relative to the sample 20 may be located at the supply spool 142, while in the embodiments having a supply spool carrier strip transfer guide 175, the vertex of the angle of change may be located at the supply spool carrier strip transfer guide 175, which may be fixed. Preferably, however, supply spool carrier strip guide 175 is present to prevent the path of the carrier strip from changing as it's supply on supply spool 142 is used up.

It can be seen that many of the specifications for the tape transport unit, such as characteristics of the adhesives selected for the sample tape 154, the distance between spools 142, 144, the amount of displacement of the carrier strip guide 170 between the "Apply" position 610 and the "Remove" position 620, and the inclusion or exclusion of elements such as a supply spool carrier strip transfer guide 175, are interrelated and impact the parameters of the separation of the carrier strip 152 from the sample tape 154. Thus, the specifications for the described features of the tape transfer unit are based on the requirements of the given microtoming.

Figure 3E:
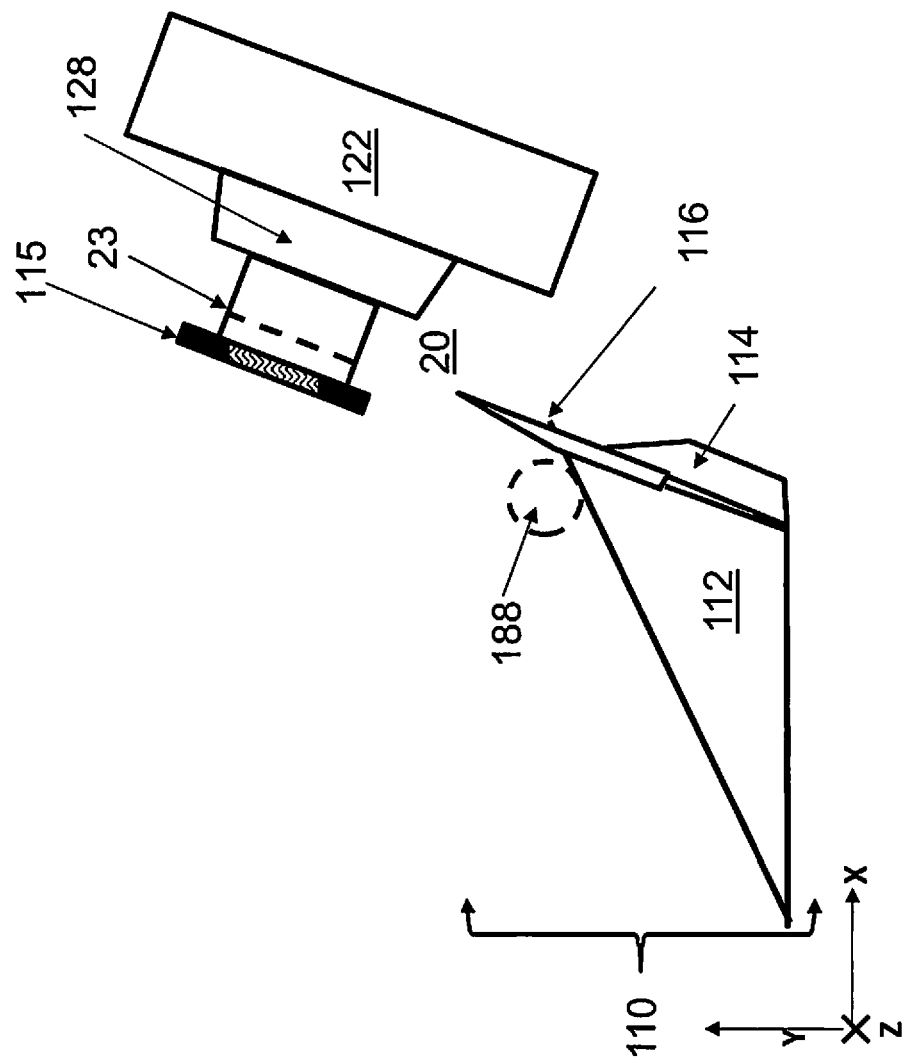

FIG. 3E shows a stage of the tape application process in which the sample 20 is prepared to be sectioned. The carrier strip 152 has been separated from the sample tape 154, which is firmly adhered to the sample 20. The chuck head 122 is in position to move through the knife blade 116 mounted on the blade handler 114 and make a single cut through the sample 20 at cut line 23 in a plane substantially parallel to a plane of the sample tape 154. In operation, the activity of microtome 100 occurs in two planes, both shown in FIG. 1A. The first plane 180, approximately 20° from vertical, is parallel to the surface of the chuck adapter 128 and defines the cutting path of the sample 20 through the knife blade 116. A second plane 190 is substantially horizontal and runs parallel to where the tape-specimen segments 25 are deposited upon being sliced from the sample 20. The cutting plane depicted may be adjusted to best match the sample and knife bevel angle desired. See, e.g., Souten, C. W., "Knife Angle in Microtomy", Leica Biosystems, Wetzlar, Germany (http://www.leicabiosystems.com/pathologyleaders/knife-angle-in-microtomy; last visited Jun. 28, 2015).

The section thickness is controlled by the adjustment controller 124. The sample 20 is cut by moving the sample 20 relative to the knife blade 116 to create a specimen segment 24. The knife blade 116 and blade handler 114 may form a T-shape when the sample 20 comes across the plane.

As the specimen segment (section) 24 is being cut by passing over the knife blade 116, the edge of the patch of sample tape 154 may be held clear. In manual operation, the operator holds on to the bottom edge with his/her fingers. In certain embodiments of the microtome 100 of the current invention, an optional roller 188 (shown in FIG. 3E in dashed lines) may be attached to the knife-block 112 to guide the patch of sample tape 154 adhered to the specimen segment 24, preventing any bending of the patch through the cutting motion. In other embodiments, the tape-specimen segments 25 may be held onto using a suction device or mechanical fingers. Optionally, to avoid manipulating individual pieces of tape-specimen segment 25 as the tape-specimen segment 25 is cut from the sample 20, a force clip (not shown) or catch mechanism (not shown) may be used to latch onto the top or bottom of the patch of sample tape 154. After the cutting motion is complete, the force clip may hold the tape-specimen segment 25 and be used to slide into a desired position or location. In one embodiment, the force clip or catch mechanism may be a conventional clip/catch such as is employed in automated tape dispensers or printer sheet rollers to pull a material along a path without touching a surface of the material. The tape-sample segment 25 may also be removed by vacuum pickup.

FIG. 3F shows a stage of the tape application process in which the microtome operation has been completed. After the chuck head 122 has moved through the knife blade 116, forming the specimen segment (cut section) 24 cut from the sample block, the specimen segment 24 is stuck to the patch of sample tape 154 (hereinafter together referred to as the tape-sample segment 25). The tape-sample segment 25 has been removed from the knife-block as described above, and is now physically out of the way of the chuck head assembly.

In stages not described in detail here, the tape-sample segment 25 may be transported for application to a glass slide with the specimen segment 24 between the patch of sample tape 154 and the slide. The slide may have an adhesive for adhering the specimen segment 24 to its surface. The slide adhesive may be catalyzed by ultra-violet light. In one embodiment, the device or mechanical fingers (not shown) that were used to hold the tape-specimen segments 25 during cutting may be used to transfer the tape specimen segment 25 to the next stage of operation (i.e., on to the glass slide for UV curing of adhesive). After curing, the patch of sample tape 154 may be carefully peeled off the mounted sample.

Figure 3G:
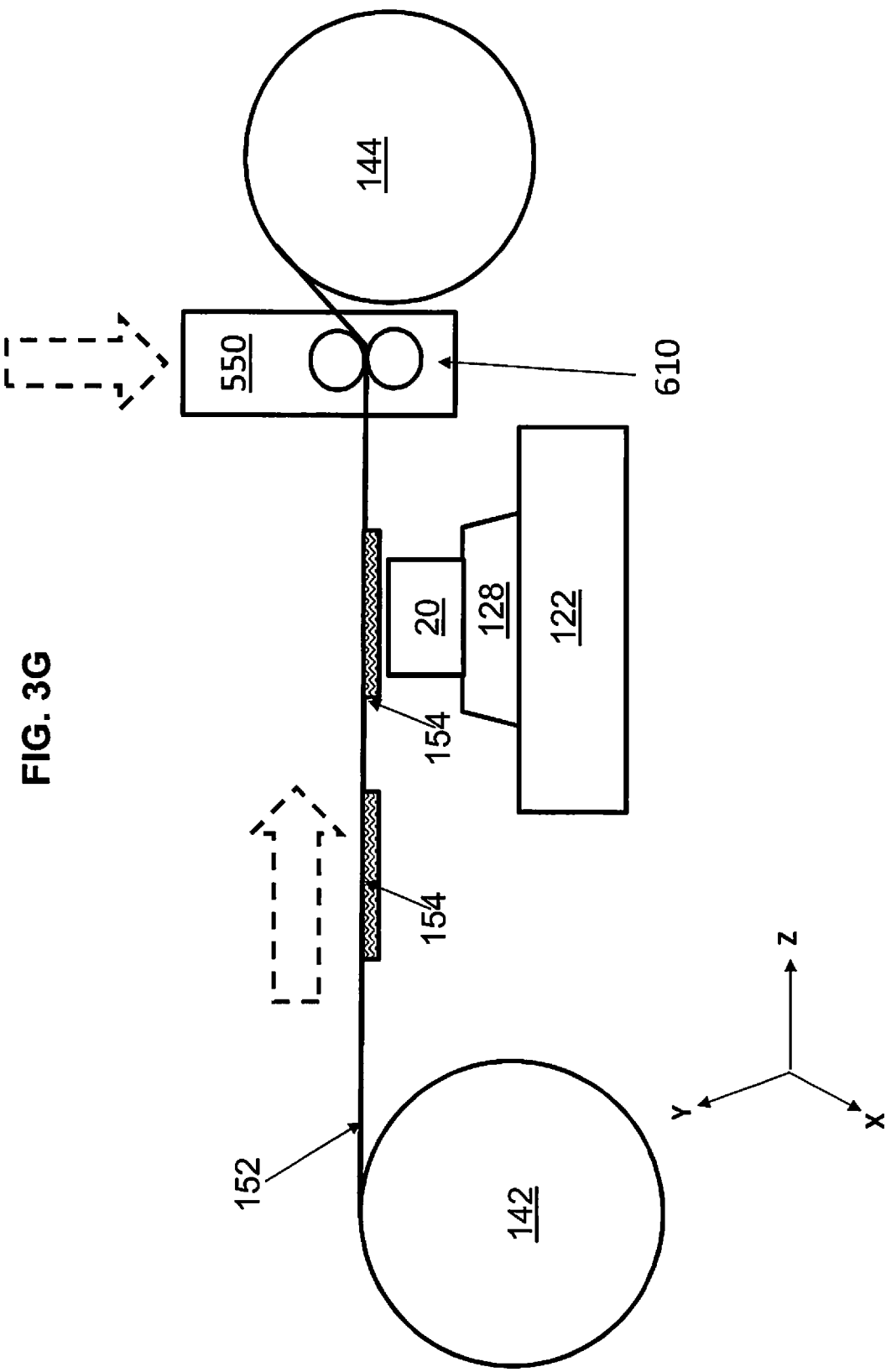

FIG. 3G shows a stage of the tape application process in which the microtome 100 is again ready for a microtome operation. The advancement mechanism 126 automatically moves the chuck head 122 forward a selected amount such that the specimen 20 is in position for the next cut section of a chosen thickness. Thus, the sample 20 is again advanced by the chuck head 122 to a microtome-ready position. The tape transport unit 140 advances and aligns a new patch of sample tape 154 above and parallel to the surface of the sample 20, and the actuator system 630 returns the carrier strip guide 170 to the "Apply" position 610.

The automated tape application process disclosed above may be operator controlled using a controller 160 inside the microtome 100, or by a controller (not shown) outside the apparatus, communicating electrically or mechanically with the herein described mechanisms.

One skilled in the art will appreciate that although only one or two of the components identified above is depicted in the Figures, any number of any of these components may be provided. Furthermore, one of ordinary skill in the art will recognize that there may be more than one tape guide or controller, and that functions provided by one or more components of any of the disclosed systems may be combined or incorporated into another component shown in the Figures.

As one of ordinary skill in the art will appreciate, one or more of units may be optional and may be omitted from implementations in certain embodiments. For example, the tape transport unit 140 may use one set of tape transport guides as in FIG. 2A, or two sets as in FIG. 2B. In addition, other tape guides may be used to guide the composite, and other elements may be used to align the sample tape patch over the sample 20. In addition, one of ordinary skill in the art will understand that the techniques and apparatus described herein are not to be limited to cryo-sectioning of biological tissues. The methods, systems, and devices described herein are equally applicable to cutting paraffin embedded biological tissue and to sectioning non-biological tissue as well.

The foregoing description has been presented for purposes of illustration. It is not exhaustive and does not limit the invention to the precise forms or embodiments disclosed. Modifications and adaptations of the invention will be apparent to those skilled in the art from consideration of the specification and practice of the disclosed embodiments. For example, it is to be understood that this invention. It is intended that the specification and examples be considered as exemplary only, with a true scope and spirit of the invention being indicated by the following claims.

The invention claimed is:

1. An automated tape transport apparatus for sectioning and transporting cut tissue sections from a sample block, the automated tape transport apparatus comprising:
   a controller;
   a tape having a first surface and a second surface opposite the first surface, the second surface being an adherence surface;
   a tape transport unit having a supply reel at an upstream end and a take up reel at a downstream end, wherein the controller is configured to control the tape transport unit to transport the tape from the supply reel for adhering the tape to the sample block for adherence of a cut tissue section from the sample block;
   a specimen holding unit for mounting the sample block with an exposed surface of the sample block outwardly facing therefrom;
   a tape application unit configured to engage with the tape to apply pressure to the first surface of the tape to press the second surface of the tape into contact with the sample block to adhere the adherence surface of the tape to the exposed surface after transport of the tape to a position adjacent and over the exposed surface;
   a specimen sectioning unit operable to section the exposed surface of the sample block for adherence of the cut tissue section to the second surface of the tape to create a sectioned sample; and
   a reciprocating actuator and a sensor configured to provide locational information of the tape, the sample block, and the tape application unit relative to each other to the controller, the controller being configured to control the reciprocating actuator based on the locational information to cause the tape application unit to apply pressure on the first surface of the tape in a first position and to cause the tape application unit to be away from the specimen holding unit in a second position.

2. The apparatus of claim 1, wherein the controller aligns the tape with the sample block so the cut tissue section can be applied to the second surface when the second surface is pressed over the exposed surface of the sample block.

3. The apparatus of claim 1, wherein the tape application unit includes a roller being configured to roll against the first surface of the tape to press the second surface of the tape on the sample block to eliminate air bubbles.

4. The apparatus of claim 1, wherein the tape application unit includes a spring-loaded roller to adhere the tape to the exposed surface of the sample block.

5. The apparatus of claim 1, further comprising a tape guide axially spaced from the tape application unit, wherein the controller is configured to control the tape guide, wherein the position of the tape guide is movable by the controller from an apply position to a remove position, the tape guide being in the apply position during advancement of the tape to align with the specimen holding unit and remaining in the apply position during movement of the tape application unit to the second position by the controller.

6. The apparatus of claim 5, wherein when the tape guide is in the apply position, an angle formed by a first line between the specimen holding unit and the supply reel and a second line between the specimen holding unit and the tape guide is about 180 degrees, whereby the tape is adjacent to and aligned with the exposed surface of said sample block and when the tape guide is in the remove position, wherein the angle formed by the first line between the specimen holding unit and the supply reel and the second line between the specimen holding unit and the tape guide is at an obtuse angle.

7. The apparatus of claim 1, wherein the controller comprises:
   (a) a processor; and
   (b) a non-transitory computer-readable medium comprising instructions for controlling the tape transport unit to dispense the tape so that a portion of the tape is adjacent to and covers the exposed surface of the sample block.

8. The apparatus of claim 1, further comprising a slide and a slide transfer station for transferring the sectioned sample from the tape to the slide.

9. The apparatus of claim 8, wherein the slide has an adhesive for adhering the sectioned sample to the slide.

10. The apparatus of claim 1, wherein the specimen sectioning unit includes a knife-block with a blade handler for holding a changeable knife blade.

11. The apparatus of claim 1, wherein the specimen holding unit comprises a chuck head and a chuck adapter for holding the sample block.

12. The apparatus of claim 1, wherein the controller comprises:
  (a) a processor; and
  (b) a non-transitory computer-readable medium comprising instructions for controlling the reciprocating actuator based on the locational information to cause the tape application unit to apply pressure on the first surface of the tape in the first position and to cause the tape application unit to be away from the specimen holding unit in the second position.

* * * * *